US007655620B2

(12) United States Patent
Kiss

(10) Patent No.: US 7,655,620 B2
(45) Date of Patent: Feb. 2, 2010

(54) USE OF ONE OR MORE METAL CARRIERS TO SELECTIVELY KILL MAMMALIAN CELLS

(75) Inventor: Zoltan Kiss, Austin, MN (US)

(73) Assignee: Cancure Laboratories, LLC, Austin, MN (US)

(*) Notice: Subject to any disclaimer, the term of this patent is extended or adjusted under 35 U.S.C. 154(b) by 88 days.

(21) Appl. No.: 11/472,763

(22) Filed: Jun. 22, 2006

(65) Prior Publication Data
US 2007/0010427 A1 Jan. 11, 2007

Related U.S. Application Data

(60) Provisional application No. 60/697,181, filed on Jul. 7, 2005.

(51) Int. Cl.
A61K 38/16 (2006.01)
C07C 325/00 (2006.01)

(52) U.S. Cl. ............................................ 514/6; 568/20

(58) Field of Classification Search ................. None
See application file for complete search history.

(56) References Cited

U.S. PATENT DOCUMENTS

| 5,783,596 | A | 7/1998 | Medford et al. |
| 6,432,452 | B1 | 8/2002 | Aylward |
| 6,756,063 | B2 | 6/2004 | Kiss |
| 2004/0171678 | A1 | 9/2004 | Kennedy |

FOREIGN PATENT DOCUMENTS

| JP | 2004277379 A | 3/2004 |
| WO | WO00/38654 | * 6/2000 |

OTHER PUBLICATIONS

Nielson et al. "Independence of domains of metallothionein in metal binding," J. Biol. Chem., 1985, 260, 8698-701.*
Gale et al. "Effects of diethyldithiocarbamate and N-methyl-N-dithiocarboxyglucamine on murine hepatic cadmium-metallothionein in vitro. " Res. Comm. Chem. Path. Pharm., 1985, 49, 423-34.*
Theocharis et al. "Metallothionein expression in human neoplasia." Histopathology, 2004, 103-18.*
Gale et al. "Effects of Diethyldithiocarbamate and N-methyl-N-Dithiocarboxyglucamine on murine hepatic cadium-metallothionein in vitro" Research Communications in Chemical Pathology and Pharmacology, 1985, 49, 423-34.*
International Search Report for PCT/US06/24608 mailed Sep. 13, 2007.
Penkowa, M. et al. Metallothionen Treatment Reduces Proinflammatory Cytokines IL-6 and TNF-alpha and Apoptotic Cell Death during Experimental Autoimmune Encephalomyelitis, Experimental Neurobiology, 2001, vol. 170, pp. 1-14.
Weitz et al., "Dissemination of tumor cells in patients undergoing surgery for colorectal cancer," Clin. Cancer Res., vol. 4, pp. 343-348, 1998.
Futoshi et al., "Molecular detection of circulating cancer cells during surgery in patients with biliary-pancreatic cancer," Am. J. Surg., vol. 177, pp. 475-479, 1999.
Camphausen, "Radiation therapy to a primary tumor accelerates metastatic growth in mice," Cancer Res., vol. 61, pp. 2207-2211, 2001.
Curtis et al., "Leukemia risk following radiotherapy for breast cancer," J. Clin. Oncol., vol. 7, pp. 21-29, 1989.
Shore, "Radiation-induced skin cancer in humans," Med. Ped. Oncol., vol. 36, pp. 549-554, 2001.
Travis et al., "Lung cancer following chemotherapy and radiotherapy for Hodgkin's disease," J. Natl. Cancer Inst., vol. 24, pp. 182-192, 2002.
Volm, "Multidrug resistance and its reversal," Anticancer Res. vol. 18, pp. 2905-2918, 1998.
Wolf et al., "Development of the novel biologically targeted anticancer agent Gefinitib: Determining the optimum dose for clinical efficacy," Clin. Cancer Res., vol. 10, pp. 4607-4613, 2004.
Kägi et al., "Biochemistry of metallothionein," Biochemistry, vol. 27, pp. 8510-8515, 1998.
Valls et al., "A new insight metallothionenin (MT) classification and evolution: The in vivo and in vitro metal binding features of homarus americanus recombinant MT," J. Biol. Chem., vol. 276, pp. 32835-32843, 2001.
Vašák et al., "Metallothioneins: new functional and structural insights," Current Opinion Chem. Biol., vol. 4, pp. 177-183, 2000.
Hunziker, "Metal removal from mammalian metallothioneins," Methods in Enzymol, vol. 205, pp. 451-456, 1991.
Kojima et al., "Amino-acid sequence of equine renal metallothioenin-1B.," Proc. Natl. Acad. Sci. USA, vol. 73, pp. 3413-3417, 1976.
Nordberg et al., "Separation of two forms of rabbit metallothionein by isoelectric focusing," Biochem. J., vol. 126, pp. 491-498, 1972.
Comeau et al., "Gram scale purification and preparation of rabbit liver zinc metallothionein," Preparative Biochem. vol. 22, pp. 151-164, 1992.
Satofuka et al., "Rapid method for detection and detoxification of heavy metal ions in water environments using phytochelatin," J. Bioscience and Bioengineering, vol. 88, pp. 287-292, 1999.
Satofuka et al., "Metal-binding properties of phytochelatin-related peptides," J. Inorganic Biochem., vol. 86, pp. 595-602, 2001.
Takagi et al., "Cellular toxicity of cadmium ions and their detoxification by heavy metal-specific plant peptides, phytochelatins, expressed in mammalian cells," J. Biochem., vol. 131, pp. 233-239, 2002.

(Continued)

Primary Examiner—Cecilia Tsang
Assistant Examiner—Christina Bradley
(74) Attorney, Agent, or Firm—Faegre & Benson LLP

(57) ABSTRACT

Compositions and methods for decreasing the viability of cells, particularly aberrant non-healthy cells, and most particularly cancer cells, are disclosed. The primary agent that causes cell death is a toxic metal atom or ion. Embodiments of the invention provide compositions and methods to ensure that the toxic metal is directed to the desired cell or tissue. In one embodiment, the metal is bound to a sulfur-rich peptide or protein carrier containing a targeting moiety. Such metal-protein complex is targeted to the selected cells or tissues to enrich the cell or tissue site with the metal-containing peptide or protein molecules followed by administering a dithiocarbonyl which carries the metal from the protein inside the cells to induce cell death.

17 Claims, 12 Drawing Sheets

OTHER PUBLICATIONS

Mehra et al., "Glutathione-mediated transfer of Cu(I) into phytochelatins," Biochem. J., vol. 307, pp. 697-705, 1995.

Toffoli et al., "Overexpression of folate binding protein in ovarian cancers," Int. J. Cancer Pred. Oncol., vol. 74, pp. 193-198, 1997.

Weitman et al., "Distribution of the folate receptor GP38 in normal and malignant cell lines and tissues," Cancer Res., vol. 52, pp. 3396-3401, 1992.

Turek et al., "Endocytosis of folate-protein conjugates: ultrastructural localization in KB cells," J. Cell Science, vol. 106, pp. 423-430, 1993.

Wang et al., "Folate-mediated targeting of antineoplastic drugs, imaging agents, and nucleic acids to cancer cells," J. Controlled Release, vol. 53, pp. 39-48, 1998.

Atkinson et al., "Conjugation of folate via gelonin carbohydrate residues retains ribosomal-inactivating properties of the toxin and permits targeting to folate receptor positive cells" J. Biol. Chem., vol. 276, pp. 27930-27935, 2001.

Beckman et al., "Superoxide dismutase and catalase conjugated to polyethylene glycol increases endotheliar enzyme activity and oxidant resistance," J.Biol. Chem., vol. 15, pp. 6884-6892, 1988.

Sawa et al., "Tumor-targeting chemotherapy by a xanthine oxidase-polymer conjugate that generates oxygen-free readicals in tumor tissues," Cancer Res., vol. 60, pp. 666-671, 2000.

Farokhzad et al., "Nanoparticle-aptamer bioconjugates: a new approach for targeting prostate cancer cells," Cancer Res., vol. 64, pp. 7668-7672, 2004.

Kukowska-Latallo et al., "Nanoparticle targeting of anticancer drug improves therapeutic response in animal model of epithelial cancer," Cancer Res., vol. 5, pp. 5317-5324, 2005.

Ibrahim et al., "Phase I and pharmacokinetic study of ABI-007, a cremophor-free, protein-stabilized, nanoparticle formulation of paclitaxel," Clin Cancer Res., vol. 8, pp. 1038-1044, 2002.

Alexiou et al., "Locoregional Cancer treatment with magnetic drug targeting," Cancer Res., vol. 60, pp. 6641-6648, 2000.

Gref et al., "Biodegradable long-circulating polymeric nanospheres," Science, vol. 263, pp. 1600-1603, 1994.

Hong et al., "Isolation of a peptide for targeted drug delivery into human head and neck solid tumors," Cancer Res., vol. 60, pp. 6551-6556, 2000.

Laakkonen et al., "A tumor-homing peptide with a targeting specificity related to lymphatic vessels," Nature Medicine, vol. 8, pp. 751-755, 2002.

Burke et al., "Citengitide targeting of $\alpha_\nu\beta_3$ integrin receptor synergizes with radioummunotherapy to increase efficacy and apoptosis in breast cancer xenografts," Cancer Res., vol. 62, pp. 4263-4272, 2002.

Arap et al., "Cancer treatment by targeted drug delivery to tumor vasculature in a mouse model," Science, vol. 279, pp. 377-380, 1998.

Nilsson et al., "Targeted delivery of tissue factor to the ED-B domain of fibronectin, a marker of angiogenesis, mediates the infarction of solid tumors in mice," Cancer Res., vol. 61, pp. 711-716, 2001.

Asai et al., "Suppression of tumor growth by novel peptides homing to tumor-derived new blood vessels," FEBS Letters, vol. 510, pp. 206-210, 2002.

Lutsenko et al., "Cytotoxic and antitumor activities of doxorubicin conjugates with the epidermal growth factor and its receptor-binding fragment," J. Drug Targeting, vol. 10, pp. 567-571, 2002.

Cortez-Retamozo et al, "Efficient cancer therapy with a nanobody-based conjugate," Cancer Res., vol. 64, pp. 2853-2857, 2004.

Halin et al., "Synergistic therapeutic effects of a tumor targeting antibody fragment, fused to interleukin 12 and to tumor necrosis factor α," Cancer Res., vol. 63, pp. 3202-3210, 2003.

Derycke et al., "Transferrin-conjugated liposome targeting of photosensitizer AIPcS$_4$ to rat bladder carcinoma cells," J. Natl. Cancer Institute, vol. 96, pp. 1620-1630, 2004.

Kasibhatla et al., "A role for transferrin receptor in triggering apoptosis when targeted with gambogic acid," Proc. Natl. Acad. Sci. USA, vol. 102, pp. 12095-12100, 2005.

Dharap et al., "Tumor-specific targeting of an anticancer drug delivery system by LHRH peptide," Proc. Natl. Acad. Sci. USA, vol. 102, pp. 12962-12967, 2005.

Kudryashov et al., "Toward optimized carbohydrate-based anticancer vaccines: Epitope clustering, carrier structure, and adjuvant all influence antibody responses to Lewis$^y$ conjugates in mice," Proc. Natl. Aca. Sci. USA, vol. 98, pp. 3264-3269, 2001.

Bradley, "Tumor targeting by covalent conjugation of a natural fatty acid to pacitaxel," Clin. Cancer Res., vol. 7, pp. 3229-32838, 2001.

Sengupta et al., "Temporal targeting of tumor cells and neovasculature with a nanoscale delivery system," Nature, vol. 436, pp. 568-572, 2005.

Mori et al., "Influence of the steric barrier activity of amphipathic poly(ethyleneglycol) and ganglioside GM1 on the circulation time of liposomes and on the target binding of immunoliposomes in vivo," FEBS Letters, vol. 284, pp. 263-266, 1991.

Harrington et al., "Effective targeting of solid tumors in patients with locally advanced cancers by radiotabled pegylated liposomes," Clin. Cancer Res., vol. 7, pp. 243-254, 2001.

Iinuma, "Intracellular targeting therapy of cisplatin-encapsulated transferrin-polyethylene glycol liposome on peritoneal dissemination of gastric cancer," Int J. Cancer, vol. 99, pp. 130-137, 2002.

Nobel et al., "Mechanism of dithiocarbamate inhibition of apoptosis: thiol oxidation by dithiocarbamate disulfides directly inhibits processing of caspase-3 proenzyme," Chem Res. Toxicol, vol. 10, pp. 636-643, 1997.

Moellering et al., "Effects of pyrrolidine dithiocarbamate on endothelial cells: protection against oxidative stress," Free Radical Biol. Med., vol. 26, pp. 1138-1145, 1999.

Trombetta et al., "Protective effects of glutathione on diethyldithicarbamate (DDC) cytotoxicity: A possible mechanism," Toxicol. Applied Pharmacol., vol. 93, pp. 154-164, 1988.

Tsai et al., "Induction of apoptosis by pyrrolidinedithiocarbamate and N-acetylcysteine in vascular smooth muscle cells," J. Biol. Chem., vol. 271, pp. 3667-3670, 1996.

Demeester, et al., "Pyrrolidine dithiocarbamate activates the heat shock response and thereby induces apoptosis in primed endothelial cells," Shock, vol. 10, pp. 1-6, 1998.

Ragione et al., "Pyrrolidine dithiocarbamate induces apoptosis by a cytochrome c-dependent mechanism," Biochem. Biophys. Res. Commun., vol. 268, pp. 942-946, 2000.

Provinciali et al., "Reactive oxygen species modulate $Zn^{2+}$-induced apoptosis in cancer cells," Free Radical Biol. & Med., vol. 32, pp. 431-445, 2002.

Kondoh et al., Requirement of caspase and p38$^{MAPK}$ activation in zinc-induced apoptosis in human leukemia HL-60 cells, Eur. J. Biochem., vol. 269, pp. 6204-6211, 2002.

Hamatake et al., "Zinc induces mixed types of cell death, necrosis, and apoptosis, in Molt-4 cells," J. Biochem., vol. 128, pp. 933-939, 2000.

Kim et al., "Sensitizing effects of cadmium on TNF-α- and TRAIL-mediated apoptosis of NIH 3T3 cells with distinct expression patterns of p53,"Carcinogenesis, vol. 23, pp. 1411-1417, 2002.

Waalkes et al., "Cadmium-induced inhibition of the growth and metastasis of human lung carcinoma xenografts: role of apoptosis, " Carcinogenesis, vol. 20, pp. 65-70, 1999.

Waalkes, "Anticarcinogenic effects of cadmium in B6C3F1 mouse liver and lung," Toxicol, Applied Pharmacol., vol. 110, pp. 327-335, 1991.

Nobel et al., "Dithiocarbamates induce apoptosis in thymocytes by raising the intracellular level of redox-active copper," J. Biol. Chem., vol. 270, pp. 26202-26208, 1995.

Kim et al., "Pyrrolidine dithiocarbamate induces bovine cerebral endothelial cell death by increasing the intracellular zinc level," J. Neurochem, vol. 72, pp. 1586-1592, 1999.

Pyatt et al., "Dithiocarbamates inhibit hematopoiesis via a copper-dependent mechanism," Biochem. Biophys. Res. Commun., vol. 274, pp. 513-518, 2000.

Van Riel et al., "Continuous administration of irinotecan by hepatic arterial infusion: A phase I and pharmacokinetic study," Clin. Cancer Res., vol. 8, pp. 405-412, 2002.

Geschwind et al., "Novel therapy for liver cancer. Direct intraarterial injection of a potent inhibitor of ATP production," Cancer Res., vol. 62, pp. 3909-3913, 2002.

Yang et al., "Convection-enhanced delivery of boronated epidermal growth factor for molecular targeting of EGF receptor-positive gliomas," Cancer Res., vol. 62, pp. 6552-6558, 2002.

Guissani et al., "Local intracerebral delivery of endogenous inhibitors by osmotic minipumps effectively suppresses glioma growth in vivo," Cancer Res., vol. 63, pp. 2499-2505, 2003.

Tomono et al., "Synergistic potentiating effects of choline phosphate and ethanolamine on insulin-induced DNA synthesis in NIH 3T3 fibroblasts," Biochem. Biophys. Res. Commun., vol. 213, pp. 980-985, 1995.

Carmichael et al., "Evaluation of tetrazolium-based semiautomated colorimetric assay: Assessment of chemosensitivity testing," Cancer Res., vol. 47, pp. 936-942, 1987.

* cited by examiner

FIGURE 1. *Structure of free amino group-containing dithiocarbamates and PDC used in the invention.*

3-aminopropylpiperidine-1-
carbodithioate. HCl
(CCK3)

Pyrrolidinecarbodithioic acid
or pyrrolidinedithiocarbamate
(PDC)

2({[(3-aminopropyl)thio]carbonothionyl}oxy)-*N,N,N*,-trimethylethanolamine-chloride 1-{[(3-aminopropyl)thio]carbonothioyl}piperidine-2-carboxilic acid 1-{[(3-aminopropyl)thio]carbonothiol}pyrrolidine-2-carboxilic acid. HCl salt 3-aminopropylpyrrolidine-1-carbodithionate. HCl salt FIG. 11. *Amino Acid Sequence for MTLP-25.*

KDCGCSGASSCNCGSGCSCSNCGSG (SEQ. ID No: 1)

Fig. 11

USE OF ONE OR MORE METAL CARRIERS TO SELECTIVELY KILL MAMMALIAN CELLS

PRIORITY CLAIM

This application claims priority from U.S. provisional application No. 60/697,181, filed Jul. 7, 2005.

FIELD OF THE INVENTION

This invention relates to compositions designed to selectively decrease the viability of targeted diseased cells, such as cancer cells, by facilitating transport of potentially toxic metals such as zinc, cadmium, copper or others, across the cell membrane.

BACKGROUND

There are many pathological conditions, particularly cancer, when aberrant tissue growth poses serious health hazard that would require rapid, selective, and effective elimination of the constituent aberrant cells. There are three major procedures in the medical practice, used alone or in combination, to accomplish this goal, i.e. surgery, radiotherapy, and chemotherapy. Each procedure, particularly when used alone, has its drawbacks. In case of cancer, a frequent problem associated with surgery is that it is often difficult to determine the tumor margin. Accordingly, the surgeon may not remove all cancer tissue thereby increasing the chances of local recurrences. Alternatively, the surgeon may remove an unnecessarily large area of uninvolved tissue. During surgery many cancer cells also disseminate into the vascular system thereby increasing the incidence of secondary cancers, particularly liver cancer [Weitz, J., Kienle, P., Lacroix, J., Willeke, F., Benner, A., Lehnert, T., Herfarth, C. and von Knebel Doeberitz, M. (1998) *Dissemination of tumor cells in patients undergoing surgery for colorectal cancer.* Clin. Cancer Res. 4, 343-348; Futoshi, M., Sonshin, T., Shoji, N., Keiichirou, U., Fumio, K., Kuniaki, A., Hiroyuki, S. and Takashi, A. (1999) *Molecular detection of circulating cancer cells during surgery in patients with biliary-pancreatic cancer.* Am. J. Surg. 177, 475-479]. Finally, in many cases the cancer is inoperable (too many tumors, inaccessible site, or risk of intervening with a vital function).

Radiotherapy, while in many cases effective, can in itself cause various cancers [Camphausen, K., Moses, M. A., Beecken, W.-D., Khan, M. K., Folkman, J. and O'Reilly, M. S. (2001) *Radiation therapy to a primary tumor accelerates metastatic growth in mice.* Cancer Res. 61, 2207-2211; Curtis, R. E., Boice, J. D. Jr., Stavall, M., Flannery, J. T. and Moloney, W. C. (1989) *Leukemia risk following radiotherapy for breast cancer.* J. Clin. Oncol. 7, 21-29; Shore, R. E. (2001) *Radiation-induced skin cancer in humans.* Med. Ped. Oncol. 36, 549-554; Travis, L. B., Gospodarowitz, M., Curtis, R. E., Clarke, E. A., Andersson, M., Glimelius, B., Joensuu, T., Lynch, C. F., van Leeuwen, F. E., Holowaty, E., Storm, H., Glimelius, I., Pukkala, E., Stovall, M., Fraumeni, J. F, Jr., Boice, J. D, Jr. and Gilbert, E. (2002) *Lung cancer following chemotherapy and radiotherapy for Hodgkin's disease.* J. Natl. Cancer Inst. 94, 182-192].

Major problems with the application of chemotherapeutic agents is that they usually do not provide a sufficient "therapeutic window", i.e. at doses that would have optimal effects on cancer growth they almost invariably attack normal tissues as well. Another problem with chemotherapy is that cells in the same tumor usually respond to a different degree, depending on how heterogeneous the tumor is. Thus chemotherapy can gradually select for less responding cancer cell populations in the tumor. Yet another problem is that chemotherapy can also induce secondary cancers [Travis, L. B., Gospodarowitz, M., Curtis, R. E., Clarke, E. A., Andersson, M., Glimelius, B., Joensuu, T., Lynch, C. F., van Leeuwen, F. E., Holowaty, E., Storm, H., Glimelius, I., Pukkala, E., Stovall, M., Fraumeni, J. F, Jr., Boice, J. D, Jr. and Gilbert, E. (2002) *Lung cancer following chemotherapy and radiotherapy for Hodgkin's disease.* J. Natl. Cancer Inst. 94, 182-192].

Finally, more often than not, cancer cells develop resistance to a wide range of drugs which will eventually make chemotherapy ineffective [Volm, M. (1998) *Multidrug resistance and its reversal.* Anticancer Res. 18, 2905-2918]. Although some agents have been developed to reverse multidrug resistance, they almost invariably exert toxic side effects, because the proteins responsible for drug resistance are also expressed and required for the normal function of some other organs [Volm, M. (1998) *Multidrug resistance and its reversal.* Anticancer Res. 18, 2905-2918].

Several other procedures are presently under development or already entered the clinical practice that provides a more selective treatment of aberrant growth. An example for this new targeted approach is Gefitinib (Iressa, ZD1839) which targets the epidermal growth factor receptor that is often highly expressed in tumor cells [Wolf, M., Swaisland, H. and Averbuch, S. (2004) *Development of the novel biologically targeted anticancer agent Gefinitib: Determining the optimum dose for clinical efficacy.* Clin. Cancer Res. 10, 4607-4613]. However, most "targeted" treatments have a relatively limited scope, because they usually target specific antigens that may not be universally present even in the same tumor due to the heterogeneous origin of tumor cells. Presently available targeted anti-cancer molecules are not sufficiently versatile for using them against a wide variety of tumor targets. Thus, there is an urgent need for chemotherapy of wider scope that can rapidly, efficiently, and at the same time specifically kill non-normal or non-healthy cells including cancer cells. Such specific "shot-gun" approach would enhance the efficacy of surgery, radiotherapy, and chemotherapy or even may render these procedures unnecessary.

SUMMARY OF THE INVENTION

Embodiments of the invention include two-carrier systems that aid in specific transport of toxic metals into targeted cells resulting in cell death. As used in this application, "targeted" cells or tissues mean non-normal or non-healthy. Such cells or tissues include cancer cells. The first carrier is a peptide or protein that binds several toxic metals but does not enter the cells or enters them only slowly. Using one of the several available methods, the first carrier-metal complex is directly implanted into or targeted to the required tissue. The second carrier is generally represented by a group of chemically synthesized compounds that have higher affinity for the metals compared to the metal-carrying peptides or proteins. Therefore, the second carrier will attract toxic metal atoms from the first carrier, already in or in the vicinity of the target tissue, and carry these metals inside the nearest cells in the target tissue thereby inducing their rapid death. In some embodiments of the invention, the second carrier molecules can be modified by fusing with targeting molecules or moieties to further enhance the accuracy of delivery of toxic metals. In other embodiments, suitable metal-bound second carrier molecules, modified by a targeting moiety, can be used to kill tumor cells in vivo independent of the first carrier.

In some embodiments, the invention provides a rapid and efficient killing of cells with a composition comprising a first peptide or protein carrier loaded with several toxic metal atoms per molecule, and a second smaller carrier molecule which can transfer the metal atoms from the first carrier into the cells. The first carrier can be any metal-binding protein or peptide from which the metal can be released at rates that are orders of magnitude greater than typical zinc-binding metalloenzymes. For such embodiments, the invention uses metallothionein (MT) and a MT-like peptide composed of 25 amino acids (MTLP-25). The second carrier can be a dithiocarbamate or any other compound that binds potentially toxic metal atoms (for example, zinc and cadmium) more strongly than the first carrier. However, the bound metal should have enough kinetic lability to allow transfer and release of the metal inside the cells. Some embodiments of the invention use second carriers, 3-aminopropylpiperidine-1-carbodithioate.HCl salt ("CCK3") or the commercially available pyrrolidinecarbodithioic acid ("PDC"; pyrrolidinedithiocarbamate). Other embodiments of the invention provide methods where cadmium- or zinc-loaded first carriers and the initially metal-free second carriers induce massive cell death when used in combination.

Some embodiments of the invention include methods, which allow preferential localization of the metal-loaded first carrier in a target tissue. These methods include implantation of peptide/protein into the target tissue by using specific devices, or fusing the peptide/protein with a targeting moiety that allows specific delivery of the complex to the target tissue. Once the accumulation of the first carrier/metal complex molecules in the target tissue reach an optimum level, subsequent application of the second carrier allows transfer of toxic metal atoms into the cells localized in the target tissue.

The invention also provides embodiments of second carriers that can be modified with a targeting molecule or moieties for improving accuracy. Both carrier components are sufficiently versatile to allow the use of a large number of targeting moieties in several combinations. For example, if a dominant target antigen is found in the target tissue (which is expressed in each cell), then it may be sufficient to modify only the peptide/protein carrier with a targeting moiety without modifying the second carrier. Alternatively, the first and second carriers may contain the same targeting molecule that will ensure delivery of toxic metals into the targeted cells with greater accuracy.

In another embodiment, the second carrier may be the mixture of two (or more) different molecules wherein the original carrier molecules are modified by two (or more) different targeting moieties targeting two (or more) different antigens in the same tumor. Targeting of a mixture of second carriers to separate target tissue is especially important when the target tissue is composed of heterogeneous cells (as is the case in most cases). These cells express both similar and different molecules (antigens), and targeting only one molecule may mean that many cells may escape either the first carrier, or the second carrier, or both. Therefore, in target tissues composed of heterogeneous cells, variants of the two-component metal carrier system that target two (or more) molecular entities will have greater efficacy than carrier systems targeting only one molecular entity. The family of the two-component carrier systems in some embodiments of the invention allows targeting of tissue including tumors, keloids, psoriatic and other aberrant tissues. Suitable variants of the two-carrier composition may be chosen depending on the specific properties of the tissue such as location, size, and resistance to killing by toxic metals as well as expression of specific cellular determinants on the cell surface.

BRIEF DESCRIPTION OF THE DRAWINGS

FIG. 11 is the amino acid sequence of the peptide labeled MTLP-25.

DETAILED DESCRIPTION OF THE INVENTION

Figure 1A:
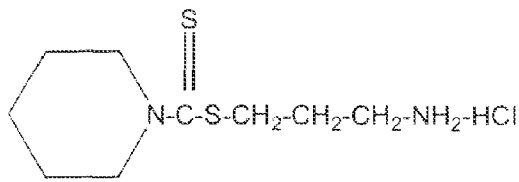
FIGS. 1A and 1B illustrate the structures of pyrrolidinecarbodithioic acid (PDC; pyrrolidinedithiocarbamate) and 3-aminopropylpiperidine-1-carbodithioate.HCl salt (CCK3) used as second carriers in embodiments of the invention. Also shown are dithiocarbamates containing an amino group that have been synthesized and tested.
Figure 1A:
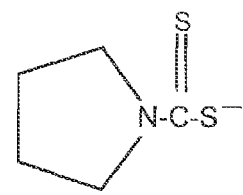
Figure 1A:
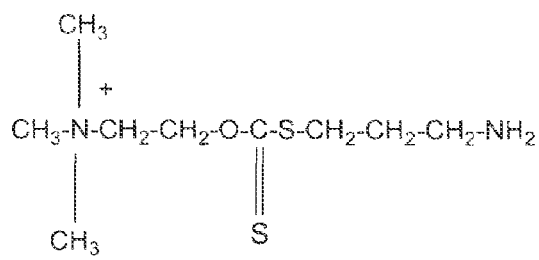
Figure 1A:
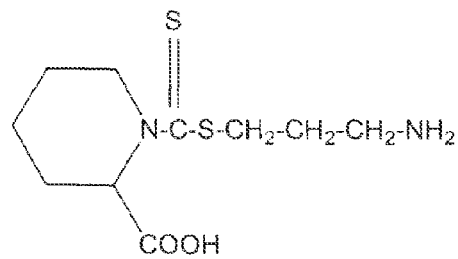
Figure 1B:
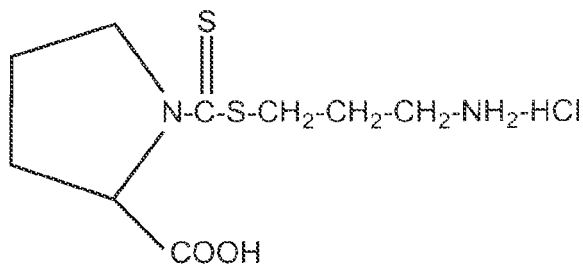
Figure 1B:
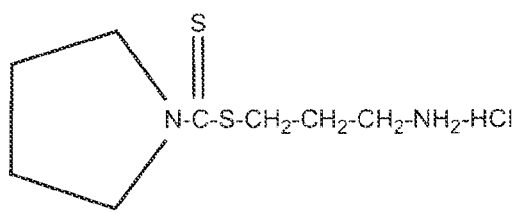

Some embodiments of the present invention may sequentially use two metal carriers to rapidly and efficiently induce cell death by toxic metals. The first carrier is a peptide or a protein that, by using various targeting methods, is preferentially enriched in the target tissue. Once the metal-loaded first carrier is at the target, the second carrier, a much smaller molecule with higher affinity for the peptide-bound metals, is released into the circulation or applied around or directly into the target tissue. The second carrier will attract first-carrier-bound toxic metal atoms and carry them inside the nearest cells causing cell death by apoptosis.

Other embodiments of the invention further provides examples of methods that can ensure preferential localization of the first carrier in the target tissue. Still other embodiments of the invention provide examples of second carriers that are designed so that they may be fused with one or more targeting molecule(s) or moieties to improve accuracy. The first and second carrier may contain the same targeting molecule. Alternatively, the second carrier may be the mixture of two or more different molecules where the original carrier molecules are modified by two or more different targeting moieties targeting two or more different antigens in the same tumor. In target tissues that are composed of heterogeneous cells, variants of the two-component metal carrier system that target two (or more) molecular entities will have greater efficacy than carrier systems targeting only one molecular entity. In such tissues, it is more likely that at least one of the two (or more) targeted entities are present in each cells, while many cells may be devoid of one of these entities. The family of two-component metal carrier systems allows targeting of tissue including tumors, keloids, psoriatic and other aberrant tissues. Suitable variants of the two-carrier composition may be chosen depending on the specific properties of the tissue such as location, size, and resistance to killing by toxic metals as well as expression of specific cellular determinants on the cell surface. Other embodiments of the invention provides using the metal-bound form of a suitable second carrier, containing one of the possible targeting moieties, to kill tumor cells in vivo independent of the first carrier.

A. Active Compositions

In some embodiments, a first carrier is a protein or a peptide that binds at least two or more atoms of one of the toxic metals with just sufficient affinity not to have them released en route to the target tissue. The metal atoms are released from these carriers at a certain low rate. However, if the peptide/protein concentration is sufficiently high, all of the released metal atoms will rapidly re-bind to this peptide/protein in the absence of a competing metal-chelating agent (i.e. there will be only intramolecular but not intermolecular metal exchange). The first carrier protein binds heavy metals, for example cadmium, zinc, mercury, copper, nickel or silver in metal-thiolate clusters.

Representatives of such first carrier proteins are various isoforms of metallothioneins (MTs) that in mammals contain 61 to 62 amino acid residues of which 20 are cysteine. However, other metalloproteins, for example superoxide dismutase, may also serve as metal donors. MTs can bind up to 7 cadmium(II) and/or zinc (II) ions, as well as 10 or more copper (I) ions [Kägi, J. H. R. and Schäfer, A. (1988) *Biochemistry of metallothionein*. Biochemistry 27, 8510-8515; Valls, M., Bofill, R., Gonzalez-Duarte, R., Gonzalez-Duarte, P., Capdevila, M. and Atrian, S. (2001) *A new insight into metallothionenin (MT) classification and evolution: The in vivo and in vitro metal binding features of homarus americanus recombinant MT*. J. Biol. Chem. 276, 32835-32843; Vašák, M. and Hasler, D. (2000) *Methallothioneins: new functional and structural insights*. Current Opinion Chem. Biol. 4, 177-183]. While the cysteine-metal(II)-cysteine crosslinks are thermodynamically stable, they undergo a continuous breaking and reforming of their non-covalent bonds which permits facile transfer of metals to suitable non-protein carriers that have higher affinity for the metal atoms. Dithiocarbamates or ammonium tetrathiomolybdate, among other compounds, work well for complete removal of zinc, cadmium, and copper from MT [Hunziker, P. E. (1991) *Metal removal from mammalian metallothioneins*. Methods in Enzymol. 205, 451-456].

Cadmium- or zinc-containing MT preparations, purified from horse kidney [Kojima, Y., Berger, C., Vallee, B. L. and Kägi, H. R. (1976) *Amino-acid sequence of equine renal metallothioenin-1B*. Proc. Natl. Acad. Sci. USA 73, 3413-3417] or rabbit liver [Nordberg, G. F., Nordberg, M., Piscator, M. and Vesterberg, O. (1972) *Separation of two forms of rabbit metallothionein by isoelectric focusing*. Biochem. J. 126, 491-498; Comeau, R. D., McDonald, K. W., Tolman, G. L., Vasak, M. and Liberatore, F. A. (1992) *Gram scale purification and preparation of rabbit liver zinc metallothionein*. Preparative Biochem. 22, 151-164], are available from Sigma-Aldrich, Inc.

In other embodiments, the first carrier contains peptides that can bind at least 3 metal atoms. The synthesis of such smaller MT-like peptide (MTLP-25), composed of 25 amino acids, is described in the "Examples" below. MTLP-25 is practically identical with a 25-mer peptide isolated from *Neurospora crassa*. However, while in the former protein the lysine residue is in the amino terminal position and glycine is in the carboxy terminal position, in the *Neurospora crassa* peptide the position of these two amino acids is reversed. MTLP-25 peptide contains 7 cysteins (C), 6 glycines (G), 1 aspartic acid (D), 1 alanine (A), 7 serine (S), 2 asparagine N), and 1 lysine (K) in the following sequence (from the amino terminal) KDCGCSGASSCNCGSGCSCSNCGSG (SEQ ID NO: 1). When fully loaded with cadmium or zinc, MTLP-25 contains 3 metal ions also in metal-thiolate clusters.

In still other embodiments, the first carriers are represented by phytochelatins (γGlutamine-Cysteine)$_n$-Glycine, n=2-11), which are small cysteine-rich peptides produced by plants, algae and fungi. They also can be synthesized by conventional methods used in peptide chemistry [Satofuka, H., Amano, S., Atomi, H., Takagi, M., Hirata, K., Miyamoto, K. and Imanaka, T. (1999) *Rapid method for detection and detoxification of heavy metal ions in water environments using phytochelatin*. J. Bioscience and Bioengineering) 88, 287-292; Satofuka, H., Fukui, T., Takagi, M., Atomi, H. and Imanaka, T. (2001) *Metal-binding properties of phytochelatin-related peptides*. J. Inorganic Biochem. 86, 595-602; Takagi, M., Satofuka, H., Amano, S., Mizuno, H., Eguchi, Y., Hirata, K. Miyamoto, K., Fukui, K. and Imanaka, T. (2002) *Cellular toxicity of cadmium ions and their detoxification by heavy metal-specific plant peptides, phytochelatins, expressed in mammalian cells*. J. Biochem. 131, 233-239].

Similar to MTs, phytochelatins are also capable of binding copper, zinc, cadmium and some other heavy metals via thiolate coordination; in fact, they have higher metal-binding capacity per cysteine than MTs [Mehra, R. K. and Mulchandani, P. (1995) *Glutathione-mediated transfer of Cu(I) into phytochelatins*. Biochem. J. 307, 697-705].

There are at least three benefits of using a peptide or protein as the first carrier of toxic metals. First, they can carry more than one metal atom, unlike most chemically synthesized metal-binding organic compounds. This property allows multiplication of effect. Second, proteins and peptides are either not taken up by the cells or taken up slowly; this allows their anchor to the cell surface and secures their access to the second carrier molecules. This property of metal/peptide complex also helps to minimize uptake of toxic metals by non-target cells en route to the target tissue. Third, MT and MT-derived peptides, but not the low-molecular weight second carriers, can be implanted into larger tumors in mini-containers (for example, in bags). Such containers are made of ultra-thin biocompatible membranes (such as regenerated cellulose) with a suitable pore size that keeps the protein inside while allowing free passage of second carriers through the pores. In some instances, such implantation technology may assure better results and at the same time may prove less costly. Depending on the use and the physiological site of application, MT or a smaller heavy metal binding peptide may be used.

In some embodiments, the second carrier is one of the suitable non-protein dithiocarbonyl or aminodithiocarbonyl molecules that can bind metals with high affinity via their dithiocarbamate or xanthogenic acid groups. This type of carrier facilitates transport of the metal atoms into cells. The best representatives for the divalent metal are the toxic cadmium and the less toxic zinc, while copper is the most effective representative of the monovalent metal group. In other embodiments, any of the divalent and monovalent metals can be substituted for cadmium and copper, as long as they bind to the first and second carrier molecules with increasing affinity and induce cell death.

The dithiocarbonyl component, typically a dithiocarbamate compound, generally has the formula: $(R_1)_m(R_2)Z$—C—(S)—S—Y wherein m is 0 or 1, but other structures can be envisioned. For example, the dithiocarbamate moiety can be inserted into fatty acid chains, or between the phosphate group and the polar headgroup, or at the end of the polar headgroup in a phospholipid molecule.

Y may be chosen from hydrogen, a methyl group, an alcohol, an acid, a pharmaceutically acceptable cation, a physiologically cleavable leaving group, a targeting moiety, or a pharmaceutically active drug, including a chemotherapeutic drug. In some embodiments, Y represents a propylamine or ethanolamine residue, which allows modification of the structure to contain, via an amide bond, a specific moiety to direct the molecule to a specific tissue.

Z may be chosen from either O or N, but if Z is O, then m=0. $R_1$ and $R_2$ may be independently chosen from hydrogen, C1-C24 straight, branched, or cyclic alkyl, alkenyl, aryl, acyl, alkaryl, aralkyl, or alkoxy fragments, optionally substituted with ester, ether, halogen, sulfate, hydroxyl, or phosphate groups. $R_1$ and $R_2$ may be optionally connected via a bridge such as —$(CH_2)n$-, wherein n is 3-8, so that the resulting structure is heterocyclic, and may be optionally substituted on any of the carbon atoms of the ring. Representative substituents include, for example, C1-C10 straight, branched, or cyclic alkyl, aryl, arylalkyl, or alkaryl groups, optionally substituted with hydroxyl, halo, phosphate, sulfate, or sulfonate groups.

Suitable dithiocarbonyl compounds include pyrrolidinecarbodithioic acid (PDC; pyrrrolidinedithiocarbamate); 3-aminopropylpiperidine-1-carbodithioate.HCl (CCK3); diethyldithiocarbamate; tetraethylthiuram disulfide (also known commonly as Disulfiram); and tricyclo-[5.2.1.$O^{2,6}$]-decyl(9[8]-xanthogenate (also known commonly as D609). Other representative dithiocarbonyl compounds are set forth in U.S. Pat. No. 5,783,596 and U.S. Pat. No. 6,756,063 incorporated herein by reference. Suitable dithiocarbonyl compounds of the present invention are 3-aminopropylpiperidine-1-carbodithioate.HCl salt (CCK3) which is commercially not available, and pyrrolidinecarbodithioic acid (PDC; pyrrolidinedithiocarbamate) which is commercially available (Sigma Chemical Company). CCK3 can be further modified in many different ways to provide additional tissue-specific targeting. PDC can be used, as it is, if no targeting of PDC molecule deemed necessary.

In some embodiments, cell death may be induced in various cell cultures by using two metal carriers of which only the peptide component (MT or the smaller MTLP-25 peptide) is loaded with metal. The metal atoms from the protein will not enter the cells (or will enter them only very slowly which is not sufficient to kill the cells) without the assistance of the low molecular weight, higher affinity carriers, such as CCK3 or PDC. These second carriers are able to attract protein-bound metal and carry the metal atoms into the nearest cells (i.e. to which the metal-protein complex is bound). Typically this two-carrier metal loaded system is suitable to kill any cell type in vitro, depending only on the amounts of components applied. CCK3 and PDC are equally effective second carriers.

In other embodiments of the present invention, the two-step procedure may be made useful by, for example, altering the peptide/protein carrier to contain a targeting moiety which ensures that the metal-protein complex will be enriched only in the chosen non-healthy tissue so that it will not cause undesirable toxic effects in normal tissues. The carrier protein/metal complex also can be implanted into the target tissue using specific porous (with a pore size between 1-3 kDa) containers such as mini-containers that keep the protein inside while allowing free transfer of low molecular weight second carriers through the pores. For example, biocompatible ultra-thin membranes with the required pore size, suitable for the preparation of peptide containers, are available commercially (for example, from Sigma Chemical Company). The technology to prepare, fill with concentrated peptide solution, close and sterilize the mini bags or similar containers is available. Similar devices, implanted for example under the skin, have been used in clinical trials with the goal of providing sustained (controlled) drug release. This method is applicable for both the full-size MT and the smaller size peptide carriers that are larger than 1 kDa, because membranes with the corresponding pore size are available on the market. Osmotic minipumps, implanted subcutaneously, represent another commercially available tool to release proteins in a controlled fashion. Alternatively, the metal complexes of carrier peptides or proteins are anchored to specific tissues (such as tumors) via various modifications of the peptides/proteins that recognize specific structures (for example, antigens) on the cell surface. The subsequently applied metal-free non-protein carriers then attract the metals from the protein and carry them into the nearest cells, i.e. cells that are present in the target tissue.

There are various ways to modify the protein/metal complex by fusing it with various targeting molecules which has the ability to specifically recognize specific structures on the surface of non-healthy cells. Representative examples of these embodiments are listed below.

Ovarian and some other cancer cells are known to overexpress the folate binding receptor proteins on the cell surface [Toffoli, G., Cernigoi, C., Russo, A., Gallo, A., Bagnoli, M. and Boiocchi, M. (1997) *Overexpression of folate binding protein in ovarian cancers*. Int. J. Cancer (Pred. Oncol. 74, 193-198; Weitman, S. D., Lark, R. H., Coney, L. R., Fort, D. W., Frasca, V., Zurawski, V. R., Jr. and Kamen, B. A. (1992) *Distribution of the folate receptor GP38 in normal and malignant cell lines and tissues*. Cancer Res. 52, 3396-3401]. Thus, by conjugating folic acid to MT or an MT-like smaller (20-30-mer) peptide it becomes possible to target the metal-loaded MT proteins/peptides to various tumor tissues overexpressing the folate receptor. Folate-protein conjugates have been described [Turek, J. J., Leamon, C. P. and Low, P. S. (1993) *Endocytosis of folate-protein conjugates: ultrastructural localization in KB cells*. J. Cell Science 106, 423-430, and references therein; Wang, S. and Low, P. S. (1998) *Folate-mediated targeting of antineoplastic drugs, imaging agents, and nucleic acids to cancer cells*. J. Controlled release. 53, 39-48, and references therein]. Conjugation of folate to a peptide can be achieved by several methods. In one embodiment, the method uses N-hydroxysuccinimide-folate to conjugate the folate directly to the amino groups present in the proteins [Atkinson, S. F., Bettinger, T., Seymour, L. W., Behr, J-P. and Ward, C. M. (2001) *Conjugation of folate via gelonin carbohydrate residues retains ribosomal-inactivating properties of the toxin and permits targeting to folate receptor positive cells*. J. Biol. Chem. 276, 27930-27935]. MT contains 8 lysines while the MTLP-25 peptide contains a terminal lysine. Thus, conjugation of folate to both MT and MTLP-25 peptide is feasible.

Many proteins are protease sensitive, which decreases their half-life in the circulation. In addition, renal clearance also contributes to decreased half-life of proteins. Finally, proteins used for clinical purpose are often highly antigenic. Conjugation of polyethylene glycol (PEG) to proteins both enhances half-life of proteins and reduces antigenicity [Beckman, J. S., Minor, R. L. Jr., White, C. W., Repine, J. E., Rosen, G. M. and Freeman, B. A. (1988) *Superoxide dismutase and catalase conjugated to polyethylene glycol increases endothelial enzyme activity and oxidant resistance*. J. Biol. Chem. 15, 6884-6892]. In addition, PEG-conjugated proteins preferentially accumulate in the tumor tissue; accordingly in case of solid tumors, PEG even alone is useful for targeted delivery of proteins [Sawa, T., Wu, J., Akaike, T. and Maeda, H. (2000) *Tumor-targeting chemotherapy by a xanthine oxidase-polymer conjugate that generates oxygen-free radicals in tumor tissues*. Cancer Res. 60, 666-671]. The structure of PEG is H—O—$(CH_2—CH_2—O)_n$—$CH_3$ with n=150 for PEG weighing 5,000 Da. The free hydroxyl of PEG is conjugated to $\epsilon$-amino groups of lysine with a bifunctional reagent such as cyanuric chloride. Because MT has 8 lysines, this provides an opportunity to simultaneously conjugate several PEG molecules and several folate molecules to the same MT molecule. Folate molecules can further enhance the accuracy of delivery of MT molecules if the target is a folate receptor-rich tumor. Such simultaneous modification of MTLP-25 peptide with folate and PEG is not feasible.

Using nanoparticles for concentrated and directed transfer of the metal-loaded MT or its derivatives to the target tissue is another example. In one embodiment, nanoparticles are made from poly(D,L-lactic acid)-block-polyethylene glycol-COOH copolymer by ring polymerization [Farokhzad, O. C., Jon, S., Khademhosseini, A., Tran, T. N. T., LaVan, D. A. and Langer, R. (2004) *Nanoparticle-aptamer bioconjugates: a new approach for targeting prostate cancer cells*. Cancer Res. 64, 7668-7672]. After activation of nanoparticles with N-hydroxysuccinimide, the MT molecules or MT-derived peptides bind to the surface of nanoparticles. This step provides for the concentration of these proteins on a transporting nanoparticle unit. The nanoparticles can be modified in many ways for targeting purpose. For example, in addition to the MT peptides, the nanoparticles can be conjugated to various 3'-$NH_2$-modified nucleic acid ligands (aptamers). As an example, an aptamer can be used that directs the nanoparticle-MT protein conjugate to the prostate cancer cells by recognizing the prostate-specific membrane antigen [Farokhzad, O. C., Jon, S., Khademhosseini, A., Tran, T. N. T., LaVan, D. A. and Langer, R. (2004) *Nanoparticle-aptamer bioconjugates: a new approach for targeting prostate cancer cells*. Cancer Res. 64, 7668-7672]. Some nanoparticles, such as polyamidoamine dendrimers, can also be conjugated to folic acid simultaneously with MT to provide better targeting to ovarian and other cancers [Kukowska-Latallo, J. F., Candido, K. A., Cao, Z., Nigevekar, S. S., Majoros, I. J., Thomas, I. T., Balogh, L. P., Khan, M. K. and Baker, J. R., Jr. (2005) *Nanoparticle targeting of anticancer drug improves therapeutic response in animal model of epithelial cancer*. Cancer Res. 5, 5317-5324]. There are numerous other targeting molecules, including the small peptides that will be discussed below, that can be bound to the nanoparticles simultaneously with the metal-loaded MT peptides.

Nanoparticle colloidal suspensions also can be made from proteins. For example, such preparations can be made from albumin that then are conjugated to paclitaxel [Ibrahim, N. K., Desai, N., Legha, S., Soon-Shiong, P., Theriault, R. L., Rivera, E., Esmaeli, B., Ring, S. E., Bedikian, A., Hortobagyi, G. N. and Ellenhorst, J. A. (2002) *Phase I and pharmacokinetic study of ABI-007, a cremophor-free, protein-stabilized, nanoparticle formulation of paclitaxel*. Clin. Cancer Res. 8, 1038-1044]. By analogy, nanoparticles also can be made from MT that then can be conjugated to various targeting molecules. Alternatively, MT and MT-derived peptides can be conjugated to albumin nanoparticles simultaneously with targeting molecules.

In other embodiments, the method for targeting is using magnetic nanoparticles [Alexiou, C., Arnold, W., Klein, R. J., Parak, F. G., Hulin, P., Bergemann, C., Erhardt, W., Wagenpfeil, S. and Lubbe, A. S. (2000) *Locoregional Cancer treatment with magnetic drug targeting*. Cancer Res. 60, 6641-6648]. Such nanoparticles consists of a colloidal dispersion formed by wet chemical methods from iron oxides and hydroxides to produce multidomain particles. In the second step, the particles are surrounded by starch polymers for stabilization and to allow chemoabsorptive binding of ligands. MT and MT-derived peptides can bind via their amino groups to the phosphate groups of the starch derivatives. However, many chemically different polymers can be used instead of starch, for example, poly(lactic-co-glycolic acid, polycaprolactone, and their copolymers [Gref, R., Minamitake, Y., Peracchia, M. T., Trubetskoy, V., Torchilin, V. and Langer, R. (1994) *Biodegradable long-circulating polymeric nanospheres*. Science 263, 1600-1603]. Magnetic nanoparticles, carrying metal-loaded MT or MT-derived peptides can be concentrated in the tumor or any other target tissue with a magnetic field that is focused on the tissue [Alexiou, C., Arnold, W., Klein, R. J., Parak, F. G., Hulin, P., Bergemann, C., Erhardt, W., Wagenpfeil, S. and Lubbe, A. S. (2000) *Locoregional Cancer treatment with magnetic drug targeting*. Cancer Res. 60, 6641-6648].

In still other embodiments, the method for targeting the metal-loaded MTLP-25 and other MT-derived peptides to tumor or other target tissues is to fuse them, using their terminal amino group, with a specific peptide via peptide bond. The same targeting peptides also can be conjugated to the MT-containing activated nanoparticles for the same purpose. In the following, several non-limiting examples of such peptides are provided. Recently a 12-mer peptide was isolated that specifically targets head and neck solid tumors. Based on its selectivity, this peptide has been proposed to serve as a targeting device for targeted drug delivery into these tumors [Hong, F. D. and Clayman, G. L. (2000) *Isolation of a peptide for targeted drug delivery into human head and neck solid tumors*. Cancer Res. 60, 6551-6556]. It is also possible to link the MT-like peptide with either a so called "tumor-homing small peptide" (CGNKRTRGC (SEQ ID NO: 2) which specifically target tumor lymphatics [Laakkonen, P., Porkka, K., Hoffman, J. A. and Ruoslahti, E. (2002) *A tumor-homing peptide with a targeting specificity related to lymphatic vessels*. Nature Medicine 8, 751-755] or the cyclic Arg-Gly-Asp (NGR) peptide, Cilengitide, which targets the $\alpha_v\beta_3$ integrin receptor and thereby the neovasculature in the tumor [Burke, P. A., DeNardo, S. J., Miers, L. A., Lamborn, K. R., Matzku, S. and DeNardo, G. L. (2002) *Cilengitide targeting of $\alpha_v\beta_3$ integrin receptor synergizes with radioimmunotherapy to increase efficacy and apoptosis in breast cancer xenografts*. Cancer Res. 62, 4263-4272]. In addition to the NGR motif, peptides that contain the RGD (Asn-Gly-Arg) motif also can serve as targeting moieties for drug delivery [Arap, W., Pasqualini, R. and Ruoslahti, E. (1998) *Cancer treatment by targeted drug delivery to tumor vasculature in a mouse model*. Science 279, 377-380]. Other possibilities for targeting various tumor tissues include the use of the ED-B domain of fibronectin [Nilsson, F., Kosmehl, H., Zardi, L. and Neri, D. (2001) *Targeted delivery of tissue factor to the ED-B domain of fibronectin, a marker of angiogenesis, mediates the infarction of solid tumors in mice*. Cancer Res. 61, 711-716], a novel ASSSYPLIHWRPWAR (SEQ ID NO: 3) peptide which binds to tumor-derived blood vessels [Asai, T., Nagatsuka, M., Kuromi, K., Yamakawa, S., Kurohane, K., Ogino, K., Tanaka, M., Taki, T. and Oku, N. (2002) *Suppression of tumor growth by novel peptides homing to tumor-derived new blood vessels*. FEBS Letters 510, 206-210], and a receptor-binding fragment of epidermal growth factor [Lutsenko, S. V., Feldman, N. B. and Severin, S. E. (2002) *Cytotoxic and antitumor activities of doxorubicin conjugates with the epidermal growth factor and its receptor-binding fragment*. J. Drug Targeting 10, 567-571].

In some embodiments, targeting molecules including antibodies recognizing specific antigens in the target tissues can also be used as targeting moiety. Nanobodies or antibody fragments, the smallest active fragments of naturally occurring single-domain antibodies, can also be used for targeting purpose; the non-limiting examples include a nanobody that recognizes the human tumor-associated carcinoembryonic antigen [Cortez-Retamozo, V., Backmann, N., Senter, P. D., Wernery, U., De Baetselier, P., Muyldermans, S. and Revets, H. (2004) *Efficient cancer therapy with a nanobody-based conjugate*. Cancer Res. 64, 2853-2857], and an antibody fragment recognizing the extradomain B of fibronectin [Halin, C., Gafner, V., Villani, M. E., Borsi, L., Berndt, A., Kosmehl, H., Zardi, L. and Neri, D. (2003) *Synergistic therapeutic effects of a tumor targeting antibody fragment, fused to interleukin 12 and to tumor necrosis factor α*. Cancer Res. 63, 3202-3210]. Similarly, any receptor-binding agonist or antagonist, or their active derivatives, can serve as a targeting moiety provided that the receptor is enriched in the target tissue. In addition to folic acid as mentioned earlier, another good example is transferrin, which binds to tumor tissues with high specificity due to the high expression of transferrin receptors in these tissues. Accordingly, transferrin has often been used as a targeting molecule [for example, Derycke, A. S. L., Kamuhabwa, A., Gijsens, A., Roskams, T., DeVos, D., Kasran, A., Huwyler, J., Missiaen, L. and de Witte, P. A. M. (2004) *Transferrin-conjugated liposome targeting of photosensitizer AlPcS$_4$ to rat bladder carcinoma cells*. J. Natl. Cancer Institute 96, 1620-1630]. In other embodiments, gambogic acid may be used for targeting the transferrin receptor. Gambogic acid is a ligand for the transferrin receptor, and it contains a carboxyl group [Kasibhatla, S., Jessen, K. A., Maliartchouk, S., Wang, J. Y., English, N. M., Drewe, J., Qiu, L., Archer, S. P., Ponce, A. E., Sirisoma, N., Jiang, S., Zhang, H. Z., Gehlsen, K. R., Cai, S. X., Green, D. R. and Tseng, B. (2005) *A role for transferrin receptor in triggering apoptosis when targeted with gambogic acid*. Proc. Natl. Acad. Sci. USA, 102, 12095-12100] which allows conjugation to MT or MTLP-25. The complex of MT/MTLP-25 and gambogic acid is expected to specifically seek out the transferrin receptor. The receptor for luteinizing hormone-releasing hormone is yet another target that can be targeted with luteinizing hormone-releasing hormone-derived short peptides [Dharap, S. S., Wang, Y., Chadna, P., Khanare, J. J., Qiu, B., Gunaseelan, S., Sinko, P. J., Stein, S., Farmanfarmaian, A. and Minko, T. (2005) *Tumor-specific targeting of an anticancer drug delivery system by LHRH peptide*. Proc. Natl. Acad. Sci. USA 102, 12962-12967] that can be conjugated to MT or MTLP-25.

In addition to target membrane proteins, other membrane components may also serve as targeting moieties. These include carbohydrates [Kudryashov, V., Glunz, P. W., Williams, L. J., Hinterman, S., Danishefsky, S. J. and Llyod, K. O. (2001) *Toward optimized carbohydrate-based anticancer vaccines: Epitope clustering, carrier structure, and adjuvant all influence antibody responses to Lewis$^y$ conjugates in mice*. Proc. Natl. Acad. Sci. USA 98, 3264-3269], and the lipid components of target cells [Bradley, M. O., Webb, N. L., Anthony, F. H., Devanesan, P., Witman, P. A., Hemamalini, S., Chander, M. C., Baker, S. D., He, L., Horwitz, B. and Swindell, C. S. (2001) *Tumor targeting by covalent conjugation of a natural fatty acid to paclitaxel*. Clin. Cancer Res. 7, 3229-3238].

Nanocells represent a special delivery system which allow temporal targeting of MT/MTLP-25 and the dithiocarbonyl compound to the target tissue. The nanocell is composed of a nuclear nanoparticle within an extranuclear pegylated-lipid envelope which preferentially accumulates in tumors [Sengupta, S., Eavarone, D., Capila, I., Zhao, G., Watson, N., Kiziltepe, T. and Sasisekharan, R. (2005) *Temporal targeting of tumor cells and neovasculature with a nanoscale delivery system*. Nature 436, 568-572]. The nanoparticle can be fabricated from the biodegradable and nonbioactive copolymer poly-(lactic-co-glycolic) acid which then can be conjugated to the amino group containing dithiocarbamate or CCK3 (one of the second metal carriers). The nanoparticles then are nucleated inside a nanoscale phospholipid bloc-copolymer envelope composed of 2,000-Da poly-(ethylene glycol) distearophosphtidylethanolamone (PEG-DSPE), phosphatidylcholine and cholesterol in an optimal ratio with MT or MTLP-25. Based on experiments with other model nanocell-bound compounds [Sengupta, S., Eavarone, D., Capila, I., Zhao, G., Watson, N., Kiziltepe, T. and Sasisekharan, R. (2005) *Temporal targeting of tumor cells and neovasculature with a nanoscale delivery system*. Nature 436, 568-572], it is expected that the first carrier, protein-metal complex will be released first followed by a slower release of the second carrier. If the first carrier, metal-protein complex is equipped with a targeting moiety, then it will reside in the target tissue awaiting the arrival of the second carrier molecules which then will carry the toxic metals inside the target cells.

The size and the three dimensional structure of the protein carrier is important to keep metals in the so-called metal-thiolate clusters not involving covalent bonds. If the cysteine peptide is too small (containing only one or two cysteines) it will bind the corresponding heavy metal via covalent bond which will not allow facile transfer of metals from the protein to the non-protein carrier. There is a wide variety of cysteine-rich proteins that can serve as metal carriers. For example, a useful protein carrier will minimally contain 10-30 amino acids of which 4-8 are cysteine molecules arranged in an order so that metal-thiolate clusters can be formed. Current synthetic processes may be used to synthesize such large peptides using solid phase or other methods. Loading of the proteins with cadmium, zinc, or any other heavy metal which binds followed by subsequent separation of loaded protein from free metal is also straightforward. Depending on the application, it may be useful to keep the size of the protein relatively small, while still maximizing its metal binding capacity, because tissue distribution of larger proteins may be less effective than that of smaller proteins. However, if the goal is to keep the protein in the circulation for a longer time, then it may be more practical to use larger peptides that will be attacked by proteases less efficiently and which will not be removed by the kidney as rapidly as smaller peptides.

The metal-binding protein itself, or the vehicle nanoparticles, may be further modified by polyethyleneglycols. These large molecules generally provide protection against destruction of peptide molecule by cells of the immune system [Mori, A., Klibanov, A. L., Torchilin, V. P. and Huang, L. (1991) *Influence of the steric barrier activity of amphipathic poly(ethyleneglycol) and ganglioside GM*1 *on the circulation time of liposomes and on the target binding of immunoliposomes in vivo*. FEBS Lett. 284, 263-266; Harrington, K. J., Mohammadtaghi, S., Uster, P. S., Glass, D., Peters, A. M., Vile, R. G. and Stewart, J. S. W. (2001) *Effective targeting of solid tumors in patients with locally advanced cancers by radiolabeled pegylated liposomes*. Clin. Cancer Res. 7, 243-254; linuma, H., Maruyama, K., Okinaga, K., sasaki, K., Sekine, T., Ishida, O., Ogiwara, N., Johkura, K. and Yonemura, Y. (2002) *Intracellular targeting therapy of cisplatin-encapsulated transferrin-polyethylene glycol liposome on peritoneal dissemination of gastric cancer*. Int. J. Cancer 99, 130-137]. Using polyethyleneglycols to coat the nanoparticles also allows addition of targeting molecules through the carboxy end.

Many variants of the MT protein and MT-derived metal carrier peptides that will allow specific transfer of toxic metal atoms into the targeted tissue may be used in embodiments of the present invention. For example, any metal binding protein that has similar characteristic compared to MT is suitable.

After the metal-carrying first carrier peptide molecules are docked to the target cells in the selected tissue, there is a need for the application of a suitable metal-free second carrier which transfers the metal from the first carrier inside the cells. Some embodiments of the invention use dithiocarbonyl molecules as second carriers. Other embodiments use, as second carriers, dithiocarbamates.

The effects of simple dithiocarbamates, mostly PDC and diethyldithiocarbamate, on cell viability have been described in many publications. These dithiocarbamates, unlike CCK3, do not possess a terminal amino group for further modification. In some cell lines and under certain experimental conditions, dithiocarbamates alone can inhibit cell death [for example, Nobel, C. S. I., Burgess, D. H., Zhivotovsky, B., Burkitt, M. J., Orrenius, S. and Slater, A. F. G. (1997) *Mechanism of dithiocarbamate inhibition of apoptosis: Thiol oxidation by dithiocarbamate disulfides directly inhibits processing of caspase*-3 *proenzyme*. Chem. Res. Toxicol. 10, 636-643; Moellering, D., McAndrew, J., Jo, H., and Darley-Usmar, V. M. (1999) *Effects of pyrrolidine dithiocarbamate on endothelial cells: protection against oxidative stress*. Free Radical Biol. Med. 26, 1138-1145]. However, in the majority of cases, dithiocarbamates alone were found to induce cell death [Trombetta, L. D., Toulon, M. and Jamall, I. S. (1988) *Protective effects of glutathione on diethyldithicarbamate (DDC) cytotoxicity: A possible mechanism*. Toxicol. Applied Pharmacol. 93, 154-164; Tsai, J. C., Jain, M., Hsich, C. M., Lee, W. S., Yoshizumi, M., Patterson, C., Perrella, M. A., Cooke, C., Wang, H., Haber, E., Schlegel, R. and Lee, M. E. (1996) *Induction of apoptosis by pyrrolidinedithiocarbamate and N-acetylcysteine in vascular smooth muscle cells*. J. Biol. Chem. 271, 3667-3670; DeMeester, S. L., Buchman, T. G., Qiu, Y., Dunnigan, K., Hotchkiss, R. S., Karl, I. E. and Cobb, J. P. (1998) *Pyrrolidine dithiocarbamate activates the heat shock response and thereby induces apoptosis in primed endothelial cells*. SHOCK 10, 1-6; Ragione, F. D., Cucciolla, V., Borriello, A., Pietra, V. D., Manna, C., Galetti, P. and Zappia, V. (2000) *Pyrrolidine dithiocarbamate induces apoptosis by a cytochrome c-dependent mechanism*. Biochem. Biophys. Res. Commun. 268, 942-946].

Incubation of cancer cells with relatively high concentrations of zinc and cadmium alone can induce their death [Provinciali, M., Donnini, A., Argentati, K., Di Stasio, G., Bartozzi, B. and Bernardini, G. (2002) *Reactive oxygen species modulate* $Zn^{2+}$*-induced apoptosis in cancer cells*. Free Radical Biol. & Med. 32, 431-445; Kondoh, M., Tasaki, E., Araragi, S., Takiguchi, M., Higashimoto, M., Watanabe, Y. and Sato, M. (2002) *Requirement of caspase and* $p38^{MAPK}$ *activation in zinc-induced apoptosis in human leukemia HL*-60 *cells*. Eur. J. Biochem. 269, 6204-6211; Hamatake, M., Iguchi, K., Hirano, K. and Ishida, R. (2000) *Zinc induces mixed types of cell death, necrosis, and apoptosis, in Molt*-4 *cells*. J. Biochem. 128, 933-939; Kim, B. J., Kim, M. S., Kim, K. B., Kim, K. W., Hong, Y. M., Kim, I. K., Lee, H. W. and Jung, Y. K. (2002) *Sensitizing effects of cadmium on TNF-α- and TRAIL-mediated apoptosis of NIH* 3*T*3 *cells with distinct expression patterns of p*53. Carcinogensis 23, 1411-1417; Waalkes, M. P. and Diwan, B. A. (1999) *Cadmium-induced inhibition of the growth and metastasis of human lung carcinoma xenografts: role of apoptosis*. Carcinogenesis 20, 65-70]. It has also been shown that cadmium inhibits the growth of lung and liver tumors and that in these organs it has specific toxicity toward previously initiated cells [Waalkes, M. P., Diwan, B. A., Weghorst, C. M., Bare, R. M., Ward, J. M. and Rice, J. M. (1991) *Anticarcinogenic effects of cadmium in B6C3F*1 *mouse liver and lung*. Toxicol. Applied Pharmacol. 110, 327-335]. Although the use of cadmium in combination with chemotherapy has been advocated [Waalkes, M. P. and Diwan, B. A. (1999) *Cadmium-induced inhibition of the growth and metastasis of human lung carcinoma xenografts: role of apoptosis*. Carcinogenesis 20, 65-70], a much safer way of exploiting the toxic effects of cadmium is by targeting it to the required tissue as described in some embodiments of the present invention.

In the presence of dithiocarbamates, cell death can be induced by much lower concentrations of toxic metals because dithicarbamates enhance cellular uptake of metals. [See, for example, Nobel, C. S., Kimland, M., Lind, B., Orrenius, S. and Slater, A. F. G. (1995) *Dithiocarbamates induce apoptosis in thymocytes by raising the intracellular level of redox-active copper*. J. Biol. Chem. 270, 26202-26208; Kim, C. H., Kim, J. H., Xu, J., Hsu, C. Y. and Ahn, Y. S. (1999) *Pyrrolidine dithiocarbamate induces bovine cerebral endothelial cell death by increasing the intracellular zinc level*. J.

Neurochem. 72, 1586-1592; Pyatt, D. W., Yang, Y., Le, A., Stillman, W. S. and Irons, R. D. (2000) *Dithiocarbamates inhibit hematopoiesis via a copper-dependent mechanism.* Biochem. Biophys. Res. Commun. 274, 513-518]. The synergistic cell killing effects of dithiocarbamates and zinc as the model metal atom have been reported in U.S. Pat. No. 6,756,063 B2 [Kiss, Z. (2004) *Methods and compositions for the treatment of human and animal cancers*].

None of the above or other publications report the synthesis and testing of an aminodithicarbonyl/aminodithiocarbamate derivative on cell viability which contains a terminal amino group suitable for further modifications by a targeting moiety. For example, after modification incorporating the propylamine group the modified dithicarbonyl/dithiocarbamate compound, such as CCK3, retains its ability to carry metals inside the cells resulting in cell death. In comparison, diethyldithocarbamate (a commercially available compound from Sigma-Aldrich, Inc.) is as effective as CCK3 in inducing cell death in the presence of cadmium or zinc, however, modification of this compound with propylamine results in significant reduction in its effects. Thus, CCK3 is regarded as a suitable type of molecule, i.e. a dithiocarbamate possessing a propylamine group that allows further modifications of the molecule for targeting purpose. The structure of other dithiocarbamates that have been described in the literature to affect cell viability does not allow further modification by targeting moieties. In addition to the propylamine group, there are many other ways to alter the dithiocarbamate structure to provide a free amino group. For example, the amino group-containing moiety can be ethanolamine, butyrylamine or other amines.

A large number of dithiocarbamates can be synthesized that, similar to 3-aminopropylpiperidine-1-carbodithioate (CCK3), contain a free amino group. Several of these compounds were synthesized and tested (in the range of 10-50 µM concentration) on cancer cells in the absence or presence of 20 µM $CdCl_2/ZnCl_2$ in comparison to CCK3, as follows. 2({[(3-aminopropyl)thio]carbonothionyl}oxy)-N,N,N-trimethylethanolamine-chloride (for structure see FIG. 1) was less effective than CCK3 in killing cancer cells. 1-{[(3-aminopropyl)thio]carbonothioyl}piperidine-2-carboxilic acid (for structure see FIG. 1) was not effective at all in the absence or presence of cadmium or zinc. Similarly, 1-{[(3-aminopropyl)thio]carbonothiol}pyrrolidine-2-carboxilic acid.HCl salt (for structure see FIG. 1) was ineffective both in the absence and presence of cadmium/zinc. The last two compounds may be ineffective because the presence of carboxyl group may interfere with proper binding of cadmium and zinc to the molecule. 3-Aminopropylpyrrolidine-1-carbodithionate.HCl salt (see structure in FIG. 1) was also significantly less effective than CCK3 despite the similarities in their structures. From this list, it appears that not every free amino group-containing dithiocarbamate can effectively kill cells in the presence of cadmium and zinc. In some of these cases the metal atom may bind to the dithiocarbamate molecule too strongly (covalently), not allowing dissociation of the metal from the molecule once inside the cell. After comparison of the above compounds with the effects of CCK3, further experiments were principally carried out with PDC and CCK3. These are representative compounds that can be the most effectively and most economically used when either no further modification of the molecule is required (PDC) or when modification with a targeting moiety is required (CCK3).

Depending on the size and location of the targeted tissue, the second carrier can be used either without or with a targeting moiety chemically attached to it. In the former case, the commercially available PDC is suitable. If targeting of the second carrier is deemed necessary to improve precision, then CCK3 is the suitable starting molecule that can be chemically combined with the targeting moiety depending on the characteristics of the target tissue. Practically the same targeting moieties, discussed in connection with targeting the protein/peptide carriers, can be used for the modification of CCK3 or a similar compound. Particularly attractive targeting molecules are small peptides that specifically bind to antigens enriched in the target tissue, because their synthesis at the required amounts and combination with the CCK3 molecules is feasible with relatively low costs. In some other cases, targeting of the folate or transferrin receptors, or any other membrane protein, with appropriate ligands may be an alternative. Finally, a targeting moiety may target non-protein membrane constituents such as carbohydrates or lipids.

The non-healthy cells in the target tissue may be heterogeneous in origin, as is often the case with human tumors. This may make it impossible to find a useful single target molecule that is expressed in each non-healthy cell. Thus, aiming in these tissues to two or three target molecules at the same time is likely to proportionally increase the chances of being able to target all non-healthy cells. Accordingly, some embodiments of the invention provide an opportunity to simultaneously use two or three different molecular versions of CCK3 (or a similar compound) that differ in the nature of the targeting units. These different forms of CCK3 can be used in a mixture at any ratio depending on the molecular characteristics of the non-healthy cells in the target tissue.

In another embodiment of the invention, metal-containing CCK3 modified by a targeting moiety is used without the first carrier to kill cells in a target tissue. In this case, the metal is bound to CCK3 prior to delivery to the desired tissue. Decisions whether metal-chelated CCK3 should be used instead of the complete two-carrier system will be based on several factors, including the size and location of the target tissue, the ease and cost of the production of the targeted first carrier, and the likelihood of the success with either approach.

When metal-complexed CCK3 is used as monotherapy, the invention provides for simultaneous application of a mixture of several versions of CCK3 that differ in the targeting moiety reflecting the heterogeneity of the non-healthy cells in the target tissue. Simultaneously aiming at more than one target in the targeted tissue increases the likelihood that the metal-chelated CCK3 molecules will reach a greater proportion of non-healthy cells and decreases the likelihood that interactions between CCK3 and normal cells will take place.

In cancer cell lines derived from solid tumors, CCK3 and PDC invariably, and with similar efficiency, killed the cells in vitro in the presence of cadmium or zinc. In some embodiments, the concentrations of CCK3 and PDC to kill cancer cells in the presence of metals are in the range of 0.1-50 µM, while in other embodiments, the concentration range is 2-20 µM. The concentration range for cadmium in some embodiments is 0.1-50 µM, while in other embodiments the concentration range is 1-10 µM. The concentration range for zinc in some embodiments is 1-100 µM, while in other embodiments the concentration range is 5-25 µM. Therapeutically effective concentrations of PDC, CCK3 or modified CCK3 and cadmium/zinc are the ones that exert maximal effects on tumors without causing significant toxicity.

Occasionally, certain cancer cell types were somewhat more sensitive to the actions of metal/CCK3 or metal/PDC than certain healthy cell types. However, in view of the insufficient differences, the data does not suggest using these combinations in vivo without proper targeting which includes adding a targeting moiety to CCK3 or applying these combinations directly into the tissue (intra-tissue application). Another possibility is, as reported in U.S. Pat. No. 6,756,063, to enhance the effects of metal/dithocarbamate complexes on cancer cells by adding additional agents, such as ethacrynic acid or dimethylethanolamine, to the treatment regimen.

In several cancer cells lines, a combination of metal-loaded MT and CCK3 effectively killed the cells after incubations for 24 hours. In some embodiments of the invention, the concentration range for cadmium/MT to kill cancer cells in vitro, in the presence of CCK3 or PDC, is 20-300 µg/ml, while in other embodiments, the concentration range is 40-120 µg/ml. The concentration range for zinc/MT, used in combination with CCK3 or PDC (in embodiments of the invention), is 40-600 µg/ml, while in other embodiments, the concentration range is 100-300 µg/ml. When used in combination with cadmium/MT in vitro, the range for CCK3 and PDC to kill cancer cells in some embodiments is 1-50 µM, while in other embodiments, the concentration range is 5-25 µM. When used in combination with zinc/MT in vitro, the concentration range for CCK3 to kill cancer cells in some embodiments of the invention is 5-200 µM, while in other embodiments, the concentration range is 10-100 µM. Therapeutically effective concentrations of metal/MT and CCK3 or PDC exert maximal effects on tumors without causing significant toxicity.

In several cancer cell lines the cadmium-loaded shorter (25 amino acid) MT-like peptide (MTLP-25) in combination with 20 µM CCK3 or PDC killed the cells in vitro after treatments for 24 h. The concentration range for these cadmium/MTLP-25 effects in some embodiments is 10-600 µg/ml, while in other embodiments, the concentration range is 50-200 µg/ml. Therapeutically effective concentrations of metal/MTLP-25 and CCK3 or PDC exert maximal effects on tumors without causing significant toxicity.

B. Methods of Use.

In some embodiments of the invention, first a metal-bound first carrier is directed to or implanted into the target tissue. After directed accumulation or implantation of the first carrier in the tissue, application of the second carrier follows. In some embodiments, a suitable formulation of the first carrier is composed of the MT/metal complex conjugated to a nanoparticle that either contains an iron core and/or a targeting molecule conjugated to the nanoparticle's surface. The nanoparticle suspension can be made in physiological saline (0.9% saline), phosphate buffered solution, or any other physiologically competent solution. In some embodiments, the delivery method of the MT-containing nanoparticle suspension is intravenous delivery. The complex is directed to the target tissue, for example a tumor, by either the targeting moiety or magnetic field, as described earlier. In other embodiments, delivery methods include subcutaneous, intraperitoneal, intratumor, intraarterial, intradermal, intramuscular, intracerebral, and aerosol delivery.

In still other embodiments, the delivery method is intraarterial when the suspension is delivered into the target tissue's blood supply. One such approach is based on the knowledge that liver tumors, in contrast to the liver tissue, are fed primarily by arterial blood. Thus, in case of liver cancer, chemotherapy is often administered by hepatic arterial infusion [van Riel, J. M. G. H., van Groeningen, C. J., Kedde, M. A., Gall, H., Leisink, J. M. A., Grula, G., Pinedo, H. M., van der Vijgh, W. J. F. and Giaccone, G. (2002) *Continuous administration of irinotecan by hepatic arterial infusion: A phase I and pharmacokinetic study*. Clin. Cancer Res. 8, 405-412; Geschwind, J.-F. H., Ko, Y. H., Torbenson, M. S., Magee, C. and Pedersen, P. L. (2002) *Novel therapy for liver cancer: Direct intraarterial injection of a potent inhibitor of ATP production*. Cancer Res. 62, 3909-3913].

In the brain, blood-brain and blood-tumor barriers greatly limit the movement of therapeutic agents from the vascular compartment into the tumor. However, methods have emerged that can help rapid distribution of the first carrier in the brain tumor tissue. Convection enhanced delivery based on applying a pressure gradient to establish bulk flow through the brain interstitium during infusion [Yang, W., Barth, R. F., Adams, D. M., Ciesielski, M. J., Fenstermaker, R. A., Shukla, S., Tjarks, W. and Caligiuri, M. A. (2002) *Convection-enhanced delivery of boronated epidermal growth factor for molecular targeting of EGF receptor-positive gliomas*. Cancer Res. 62, 6552-6558]. Local intracerebral delivery by osmotic minipumps is another effective method to administer the first carrier close to the brain tumor tissue [Giussani, C., Carrabba, G., Pluderi, M., Lucini, V., Pannacci, M., Caronzolo, D., Costa, F., Minotti, M., Tomei, G., Villani, R., Bikfalvi, A. and Bello, L. (2003) *Local intracerebral delivery of endogenous inhibitors by osmotic minipumps effectively suppresses glioma growth in vivo*. Cancer Res. 63, 2499-2505]. A commercial osmotic minipump may also be implanted subcutaneously if the target tissue is located outside the brain.

Another suitable formulation is when the first carrier is an MTLP-25 peptide or another MT-derived peptide that is bound to a nanoparticle and delivered to the target tissue as described above. Yet another suitable formulation is when the MT/metal complex or the MT-derived peptide/metal complex is not bound to a nanoparticle; instead, it is modified to contain a targeting moiety directly attached to the protein. A further suitable formulation involves nanocells as described earlier, which allows simultaneous delivery followed by temporal release of MT/MTLP-25 and the dithiocarbonyl compound in that order. Other available methods for the preparation of protein solutions and their administration may be used as well.

The metal/protein complex can be used only with proper targeting to avoid non-specific shorter-term or longer-term toxic effects. However, there may be instances when the synthesis of a targeting moiety and/or its fusion with the metal/protein complex is not feasible or may prove prohibitively expensive. As such, other embodiments of the invention include implantation of the metal/protein complex into the tumor tissue. Mini-containers (for example, bags, in the 2-10 mm range), made from ultrathin biocompatible membranes with appropriate pore size that retains the metal/protein while allowing free transfer of the second carrier through the pores, can be used for implantation. The ultrathin biocompatible membranes for this purpose are commercially available (for example, from Sigma Aldrich). Preparation, filling, closure, and sterilization of various mini-containers are procedures that are known for similar applications.

The metal complex of the large peptide/protein carrier is modified chemically by a targeting moiety or bound inside or outside to a specific carrier (that may also be equipped with a targeting moiety) and typically applied via a systemic route such as, for example, the tumor's blood supply. A certain time period, the length of which depends on the anatomical location of the aberrant tissue and the distance from the site of application, is required for optimal targeting of this metal/large carrier complex. Then, the second carrier is released into the circulation as close to the tumor site as possible, which will transfer the metal ions from the larger carrier into the target cells. In some embodiments, within eight hours of applying the second carrier, 60-100% of aberrant cells in the targeted tissue will be dead; in other embodiments, preferably 90-100% of aberrant cells will die within 24 hours of applying the second carrier. In other embodiments, systemic treatment exposes 50%, in other embodiments, 90%, and still other embodiments, 100% of the cells in the aberrant tissue to effective doses of the metal-large carrier complex and the second carrier. The dosage, timing, sequence, the number of treatments and methods of application of the components of the two-carrier system will depend, in part, on the type, size, and response rate of the target tissue.

When used either as a monotherapy as a metal complex or as a component of the two-carrier system, a preferred application of the small carriers, exemplified by CCK3 and PDC, is direct injection into the aberrant tissue such as a tumor. Such application may be performed once, or maybe repeated several times over a period of time, depending on the test results (rapid microscopic analysis of tumor cells). This application method concentrates the toxic metal in the target tissue and minimizes their distribution in other parts of the body. To provide additional specificity, CCK3, modified with a targeting moiety may be used for intratissue application.

Another application is administering metal-free CCK3/PDC (as a component of the two-carrier system), or metal-chelated CCK3/PDC (if used for monotherapy) systemically into the tumor's blood supply in order to expose the tumor to a significantly larger dose than the healthy tissues. As an example, in the case of liver cancer the application can be intraarterial as discussed earlier. When either unmodified CCK3 or PDC is used as a component of the two-carrier system, they may be delivered orally (formulated as tablets or components of gel capsules), subcutaneously, intradermally, or intraperitonially. When CCK3 (or a similar compound) is modified with a targeting moiety and is used independent of the peptide/protein component of the two-carrier system, their typical application is intravenous, intraarterial, intracerebral, intraperitoneal or subcutaneous, although in some cases oral application may also be feasible. Alternatively, for systemic application these compounds may be enclosed in polyethyleneglycol-coated immunoliposomes or other delivery systems or formulations. In some embodiments of the invention, both intra-tissue and systemic treatment exposes 50%, in other embodiments, 90%, and still other embodiments, 100% of the cells in the aberrant tissue with an effective dose of CCK3, PDC, or a similar compound. The dosage and the number of treatments will depend, among other factors, on the type, location and response rate of the target tissue as well as the method of administration of these compounds.

EXAMPLES

Example 1

Synthesis of Non-protein Carrier
3-aminopropylpiperidine-1-carbodithioate.HCl salt
(CCK3)

20.43-g (0.24 mol) piperidine was dissolved in a mixture of 8.0-g (0.2 mol) of NaOH and 35-ml of water and the mixture was cooled to 0-2° C. Then 0.2 mol of $CS_2$ was added dropwise over one hour period with intensive stirring of the mixture. This was followed by the stirring of the mixture for four additional hours at room temperature (22° C.). The precipitated N-piperidinedithiocarbamic acid was dissolved in 200 ml of water, filtered, mixed with 300 ml of acetone, and kept overnight at 4° C. The white precipitate was filtered, washed twice with ice-cold acetone, and dried. Seventeen g of N-piperidinedithiocarbamic acid was dissolved in 20-ml of water and slowly mixed with 0.011 mol (in 10 ml water) of 3-chloropropylamine (HCL salt). After stirring the mixture for an additional 4 hours period, the mixture was kept overnight at 4° C. The precipitated CCK3 compound was filtered, washed with 2×10 ml of ice-cold water, and then dried. The yield was usually in the range of 1.3-1.5-g. CCK3 can be dissolved in water or first in dimethylsulfoxide followed by dilution with water.

Example 2

Preparation of MTLP-25

The sequence of the MTLP-25 peptide is as follows:

(SEQ ID NO: 1)
Ac-K($\epsilon$-$NH_2$)-DCGCSGASSCNCGSGCSCSNCGSG-$NH_2$.

This structure allows the use of terminal $NH_2$ group to bind selected targeting units via amide bond. The peptide was synthesized on MBHA resin (0.56 mmol/g) in 0.1 mmol quantity with Boc-strategy by automatic peptide synthesizer (AB 410). The tri-functional amino acids were protected as follows: Boc-Cys(Mbzl), Boc-Ser(Bzl) and Boc-Lys(Fmoc). For coupling, the DCC/HOBt method was used. After the coupling was complete, the protected peptide, still on the resin, was removed from the synthesizer. The N-terminal amino group was acetylated with the acetyl-OPFP activated ester and the $\epsilon$-amino group was liberated from the Fmoc group of the N-terminal lysine. In the next step, the side function groups and the peptide were removed from the resin by using HF and scavengers. The solution, which had the pH of 2.0, was divided into three parts. One part was lyophilized, while the other two parts were treated at room temperature with two molar equivalents of Cd—$Ac_2$ or Zn—$Ac_2$. Both fractions were lyophilized and re-dissolved, followed by the removal of non-bound metal by Sephadex G-25 chromatography and subsequent dialysis. Binding of cadmium and zinc to the peptide was verified and quantitated by MS/MS- and CD-spectroscopy. With both methods, the corresponding metal-peptide complexes contained approximately three ions of cadmium or zinc per one peptide molecule. This description, including the specific technical expressions used, provides sufficient information to enable a trained peptide chemist to synthesize MT-like peptides of variable lengths unloaded or loaded with the corresponding metal.

Example 3

Demonstration and Quantification of Cell Death

Cells which lost viability do not synthesize DNA. To quantify cell death, around the time when significant and characteristic morphological changes took place, cells were pulse-labeled for 30 min. with [$^3$H]thymidine to measure DNA activity as described in [Tomono, M. Crilly, K. S. and Kiss, Z. (1995) [*Synergistic potentiating effects of choline phosphate and ethanolamine on insulin-induced DNA synthesis in NIH 3T3 fibroblasts*. Biochem. Biophys. Res. Commun. 213, 980-985]. Also, cells were collected by making cell suspensions with trypsin, followed by re-plating using fresh tissue culture medium. If no viable cells were obtained after 1 week in culture, it meant that the cells at the time of re-plating were practically 100% dead. Survival values obtained with untreated cells were considered 100%. For the determination of relative number of viable cells after treatments, the MTT assay was used. This colorimetric assay is based on the ability of living cells, but not dead cells, to reduce 3-(4,5-dimethyl thiazol-2-yl)-2,5-diphenyltetrazolium bromide [Carmichael, J, De Graff, W. G., Gazdar, A. F., Minna, J. D. and Mitchell, J. B. (1987) *Evaluation of tetrazolium-based semiautomated calorimetric assay: Assessment of chemosensitivity testing*. Cancer Res. 47, 936-942]. For this assay, cells were plated in 96-well plates, treated as described for Example 4, and the MTT assay was performed both in untreated and treated cell cultures. MTT assay also was performed at the time when the treatment was started; this allows assessment of the proliferation rates in the control and treated cell cultures.

Examples Relating to the Combined Effects of Cadmium or Zinc and CCK3 or PDC on the Viability of Normal and Cancer Cells All cell lines used and tested in this and the following examples were purchased from the American Type Culture Collection (Rockville, Md.).

Example 4

Figure 2:
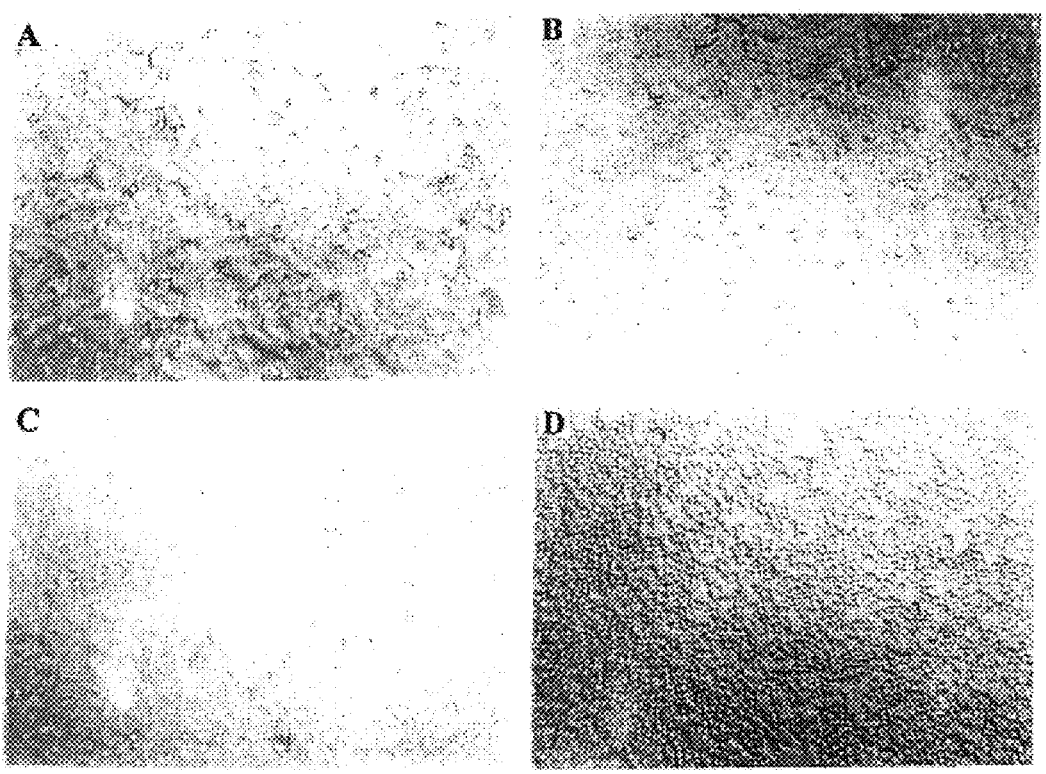
FIG. 2 is an image demonstrating in some embodiments of the invention that CCK3 (5 µM) and cadmium (10 µM) in combination effectively killed the T47D breast cancer cells (estrogen receptor-positive) after treatment for 4 hours (D). Compared to the control (A), CCK3 (B) or cadmium (C) had no effects on cell morphology when used alone.

Demonstration that CCK3 and Cadmium in Combination Effectively Kill the Estrogen Receptor Positive T47D Human Mammary Gland Ductal Carcinoma Cells T47D Cells were cultured in RPMI 1640 cell culture medium (see Gibco Catalogue) supplied with 2 mM L-glutamine, 10 mM Hepes, 1 mM sodium pyruvate, 4.5 g/L glucose, 1.5 g/L sodium bicarbonate, 0.2 I.U. bovine insulin/ml, and 10% fetal bovine serum. The medium was changed for fresh 10% serum-containing medium 2 hours prior to treatments. For the treatments, the cells were incubated in triplicate in 12-well plates. A typical experiment is shown in FIG. 2. The cells were untreated (FIG. 2A) or treated with 5 μM CCK3 alone (FIG. 2B), 10 μM cadmium alone (FIG. 2C), or 5 μM CCK3 and 10 μM cadmium in combination (FIG. 2D) for 4 hours in 10% serum-containing medium when the photographs were taken. Only the combined treatment (FIG. 2D) killed the cells as clearly indicated by cell morphology (cell rounding) typical of cells that die by the apoptotic form of cell death (see U.S. Pat. No. 6,756,063 incorporated herein by reference). When CCK3+cadmium-treated (4 hours) cells were washed and incubated in fresh medium, no viable cells were found with the trypan blue exclusion assay after a one week period. Finally, cells were incubated with [$^3$H]thymidine (1 μCi/ml) during the last 30 min of treatment to determine DNA synthesis. Cadmium and CCK3 decreased DNA synthesis by 13 and 8% respectively, while in combination they had practically 100% inhibitory effect. All these experiments indicated that CCK3 and cadmium can effectively and rapidly kill the T47D cells.

Example 5

Figure 3:
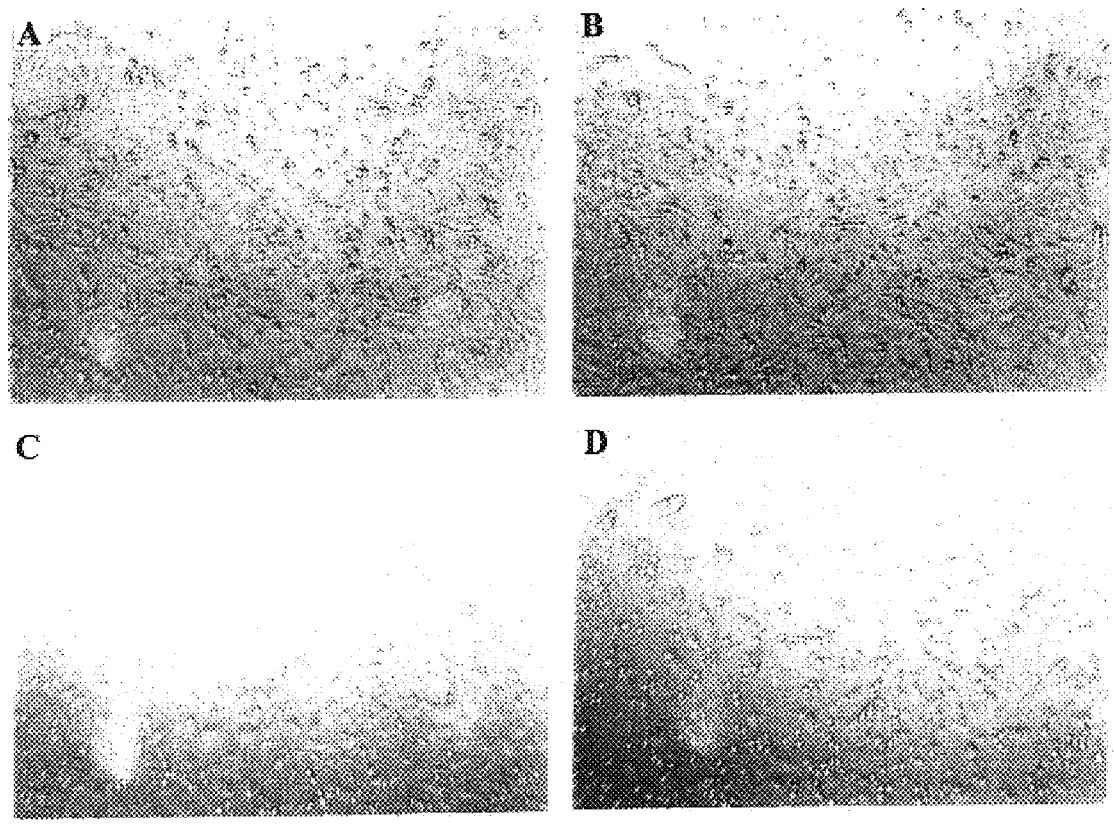
FIG. 3 is an image demonstrating in some embodiments of the invention that CCK3 (5 µM) and cadmium (10 µM) in combination effectively killed the MDA-MB-231 breast cancer cells (estrogen receptor negative) after treatment for 60 min (D). Compared to the control (A), CCK3 (B) or cadmium (C) had no effects on cell morphology when used alone.

Demonstration that CCK3 and Cadmium in Combination Effectively Kill the Estrogen Receptor Negative MDA-MB-231 Human Mammary Gland Adenocarcinoma Cells MDA-MB-231 cells were cultured in Leibovitz's L-15 medium and 10% fetal bovine serum; the medium was changed 2 hours prior to treatments. For the treatments, cells were incubated in triplicate in 12-well plates. A typical experiment with these cells is illustrated in FIG. 3. The cells were untreated (FIG. 3A) or treated with 5 μM CCK3 (FIG. 3B), 10 μM cadmium (FIG. 3C), or 5 μM CCK3+10 μM cadmium (FIG. 3D) for 60 min in 10% serum-containing medium. Only the combined treatment (FIG. 3D) killed the cells as indicated by the altered (cell rounding) cell morphology. When CCK3+cadmium-treated (60 min) cells were washed and incubated in fresh medium, no viable cells were found after a subsequent one week examination period as determined by the trypan blue exclusion assay. In some experiments, cells were also incubated with [$^3$H]thymidine (1 μCi/ml) during the last 30 min of treatment to determine DNA synthesis. Cadmium and PDC decreased DNA synthesis by 6 and 12%, while in combination they had 100% inhibitory effect.

Examples Showing that the Combined Treatments with CCK3 or PDC and Relatively Low Amounts of Metal Loaded MT (60 μg/ml) for 24 Hours Significantly Decrease the Viability of Normal and Cancer Cells

Example 6

CCK3 and Cadmium/MT in Combination are Toxic to Cells

Figure 4:
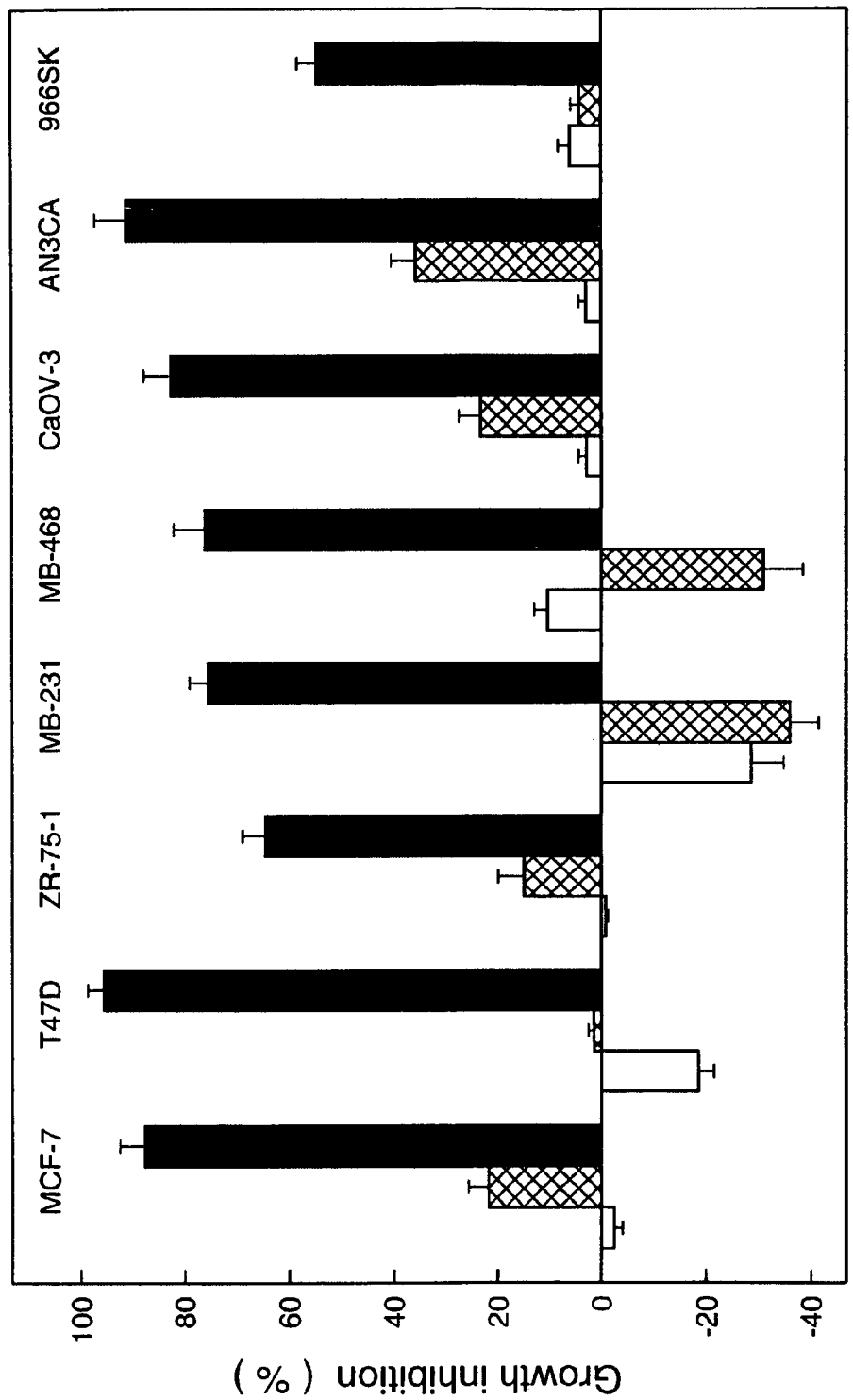
FIG. 4 is a diagram demonstrating in some embodiments of the invention that treatments of various cancer and normal cells with CCK3 (10 µM) plus cadmium-loaded metallothionein (cadmium/MT) (60 µg/ml) for 24 hour invariably reduced cell viability (■), black bar. Also shown are the individual effects of CCK3 (□), white bar, and cadmium/MT (▨), crosshatch bar, that always remained significantly smaller than the combined effects of CCK3 and cadmium/MT.

MCF-7 estrogen receptor positive human breast carcinoma cells and CaOV-3 human ovarian adenocarcinoma cells were grown in Dulbecco's modified Eagle's medium containing 4 mM L-glutamine, 1.5 g/L sodium bicarbonate, 4.5 g/L glucose, 1 mM sodium pyruvate and 10% fetal bovine serum. T47D human mammary gland ductal carcinoma cells and ZR-75-1 estrogen receptor positive human mammary gland ductal carcinoma cells were cultured in RPMI 1640 medium as indicated above. MB-468 and MB-231 human mammary gland adenocarcinoma cells were maintained in Leibovitz's L-15 medium as described above. AN3CA human endometrial adenocarcinoma and 966 SK normal human skin fibroblasts were cultured in Eagles's minimum essential medium supplemented with 0.1 mM non-essential amino acids and 10% fetal bovine serum. The preparation of MT (from Sigma-Aldrich, Inc.) used in this experiment contained about 4 ions of cadmium and only about 0.3 ions of zinc per MT molecule. Confluent or near-confluent cultures of various cancer and human normal 966 SK skin fibroblasts were incubated in 96-well plates in 10% serum-containing medium for 24 h in the absence (0% inhibition) or presence of 10 μM CCK3 (□), white bar, or 60 μg/ml of cadmium/MT (▧), crosshatch bar, or 10 μM CCK3+60 μg/ml of cadmium/MT (■), black bar. The MTT assay was used for the determination of relative cell numbers. Data are illustrated in FIG. 4 as rates of growth inhibition (maximum inhibition=100%) in comparison to values without treatment. The error bars indicate S.D. (n=8). Of the seven different types of human cancer cells examined, as listed above, 10 μM CCK3 and 60 μg/ml of cadmium/MT in combination killed 90-100% of the estrogen receptor positive breast cancer T47D and MCF-7 cells as well as the endometrial cancer AN3CA cells, and 70-80% of the estrogen receptor negative breast cancer MDA-MB-231 and MDA-MB-468 cells as well as ovarian cancer CaOV-3 cells (FIG. 4). The estrogen receptor positive breast cancer ZR-75-1 cells and normal human skin fibroblasts (966 SK) showed somewhat greater survival after the combined treatments with CCK3 and cadmium/MT (FIG. 4). In AN3CA cells, cadmium/MT alone was about 40% as effective as cadmium/MT+CCK3; in other cell lines cadmium/MT alone was ineffective or much less effective than in combination with CCK3 (FIG. 4). In some cases (MB-231 and MB-468 cells), cadmium/MT alone enhanced the proliferation of cells. The powerful effects of CCK3 in the presence of cadmium-loaded MT indicate that it is capable of effectively transferring cadmium atoms from MT inside the cells. In some experiments, cells were also incubated with [$^3$H]thymidine (1 μCi/ml) during the last 60 min of the 24 hours treatment period to determine DNA synthesis; cadmium/MT alone and in the presence of CCK3 decreased DNA synthesis by 5-38% and 91-100%, respectively, in the various cell lines. In another experiment, these same treatments (using the same concentrations of agents) were also performed for 8 hours followed by taking pictures and performing the MTT assay. The combined inhibitory effects of cadmium/MT+CCK3 always remained below 30%.

Example 7

Figure 5:
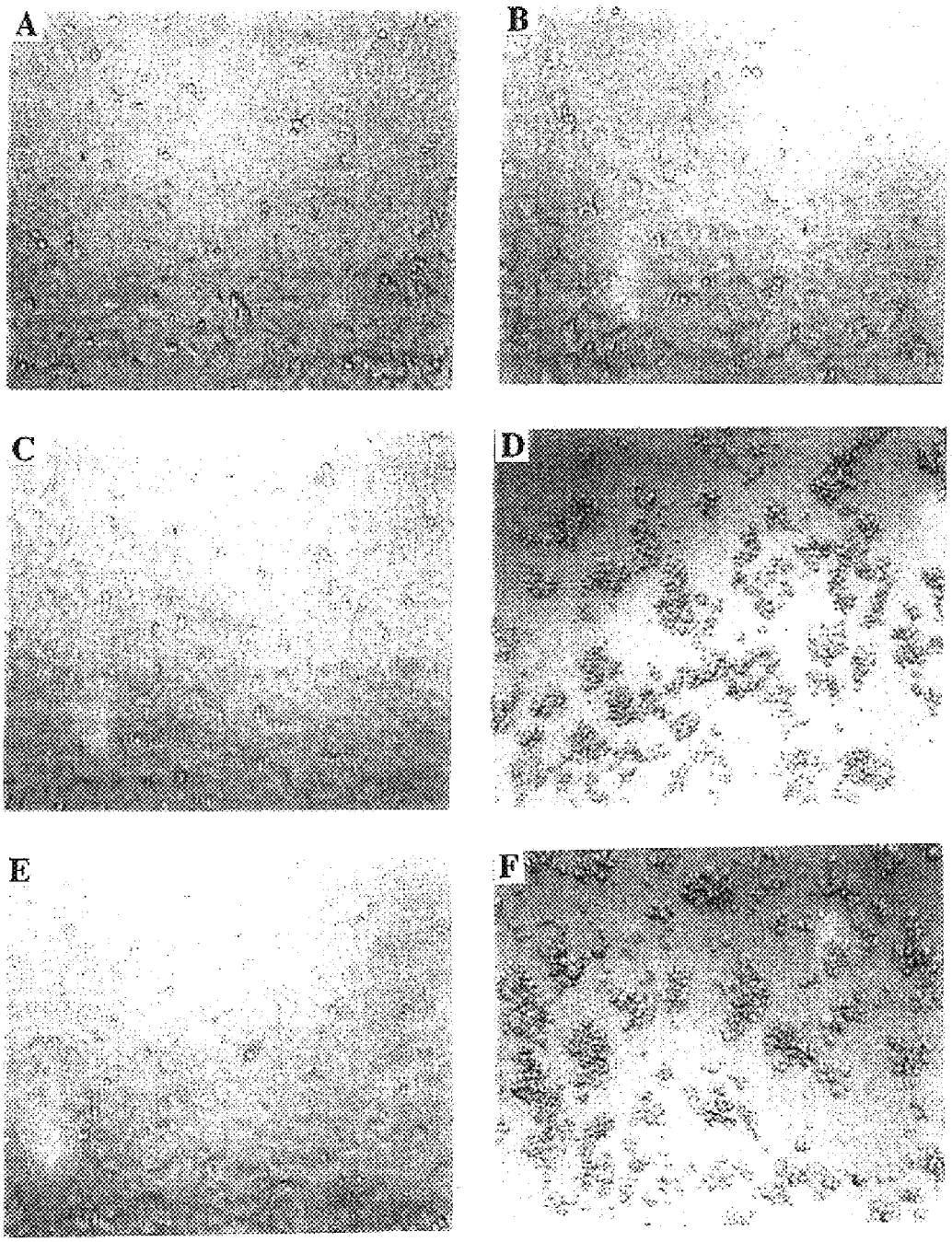
FIG. 5 is an image demonstrating in some embodiments of the invention that PDC (10 µM) and cadmium/MT (60 µg/ml) (D) or a much higher concentration of zinc/MT (240 µg/ml) (F) in combination induced the death of T47D cells after treatments for 24 hours. Compared to the untreated control (A), single treatments with PDC (B), cadmium/MT (C) or zinc/MT (E) all failed to significantly alter cell morphology.

PDC and Cadmium/MT or Zinc/MT in Combination Induce the Death of Estrogen Receptor Positive Human Breast Cancer T47D Cells The cadmium/MT used in this experiment contained 5 atoms of cadmium and 1 atom of zinc, while the zinc/MT contained 5 atoms of zinc and 1 atom of cadmium per one MT molecule. For the treatments, the cells were incubated in triplicate in 12-well plates. A typical experiment is illustrated in FIG. 5. T47D cells were incubated in 10% serum-containing for 24 h in the absence (FIG. 5A) or presence of 10 μM PDC (FIG. 5B), 60 μg/ml of cadmium/MT (FIG. 5C), 60 μg/ml of cadmium/MT+10 μM PDC (FIG. 5D), 240 μg/ml of zinc/MT (FIG. 5E), or 240 μg/ml of zinc/MT+10 μM PDC (FIG. 5F). Both MT preparations effectively killed the cells in the presence, but not in the absence, of PDC. In a similar experiment, the trypan blue exclusion assay confirmed that while cadmium/MT, zinc/MT and PDC alone had practically no effects on cell death, both cadmium/MT+PDC and zinc/MT+PDC killed 100% of cells. It should be noted that 120 μg/ml of zinc/MT+PDC killed only about 20% of cells after treatments for 24 hours (not shown). Thus, cadmium/MT in combination with PDC is clearly more effective in killing the T47 breast cancer cells than zinc/MT+PDC.

Example 8

Figure 6:
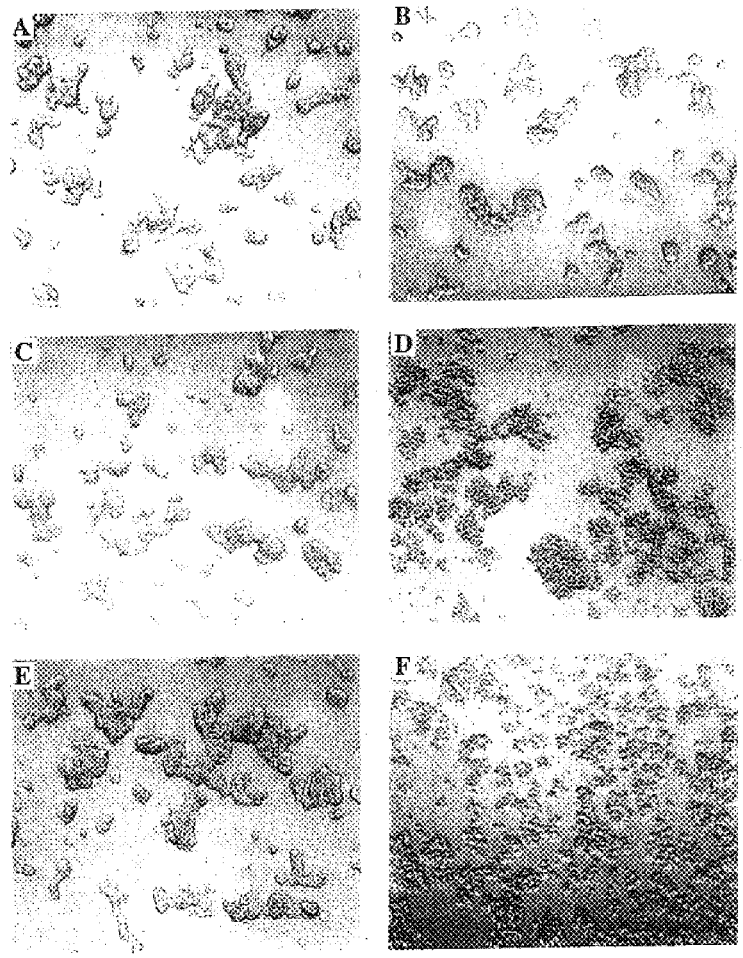
FIG. 6 is an image demonstrating in some embodiments of the invention that CCK3 (10 µM) and cadmium/MT (60 µg/ml) (D) or CCK3 and a higher (240 µg/ml) concentration of zinc/MT (F) in combination induced the death of estrogen receptor positive human breast cancer ZR-75-1 cells after treatments for 24 hours. Compared to the untreated control (A), single treatments with CCK3 (B), cadmium/MT (C) or zinc/MT (E) all failed to significantly alter cell morphology.

CCK3 and Cadmium/MT or Zinc/MT in Combination Induce the Death of Estrogen Receptor Positive Human Breast ZR-75-1 Cells ZR-75-1 cells were cultured in triplicate in 12-well plates in the medium described in Example 4. The cadmium/MT contained 5 atoms of cadmium and 1 atom of zinc, while the zinc/MT contained 5 atoms of zinc and 1 atom of cadmium per one MT molecule. ZR-75-1 cells were incubated in 10% serum-containing medium for 24 h in the absence (FIG. 6A) or presence of 15 μM CCK3 (FIG. 6B), 60 μg/ml of cadmium/MT (FIG. 6C), 60 μg/ml of cadmium/MT+15 μM CCK3 (FIG. 6D), 240 μg/ml of zinc/MT (FIG. 6E), or 240 μg/ml of zinc/MT+15 μM CCK3 (FIG. 6F). Both MT preparations effectively killed the cells in the presence, but not in the absence, of CCK3. In a similar experiment, the trypan blue exclusion assay confirmed that while cadmium/MT, zinc/MT and CCK3 alone had practically no effects, both cadmium/MT+CCK3 and zinc/MT+CCK3 killed 100% of cells. It should be noted that 120 μg/ml of zinc/MT and CCK3 in combination killed only 20-25% of cells (not shown). This again indicates that the CCK3+cadmium/MT combination is clearly more effective than the CCK3+zinc/MT combination.

Examples Showing that Combined Treatments with CCK3 or PDC and an Increased Dose of Cadmium/Mt (120 μg/ml) for Only 8 Hours are Sufficient to Kill Most Cancer Cells

Example 9

Figure 7:
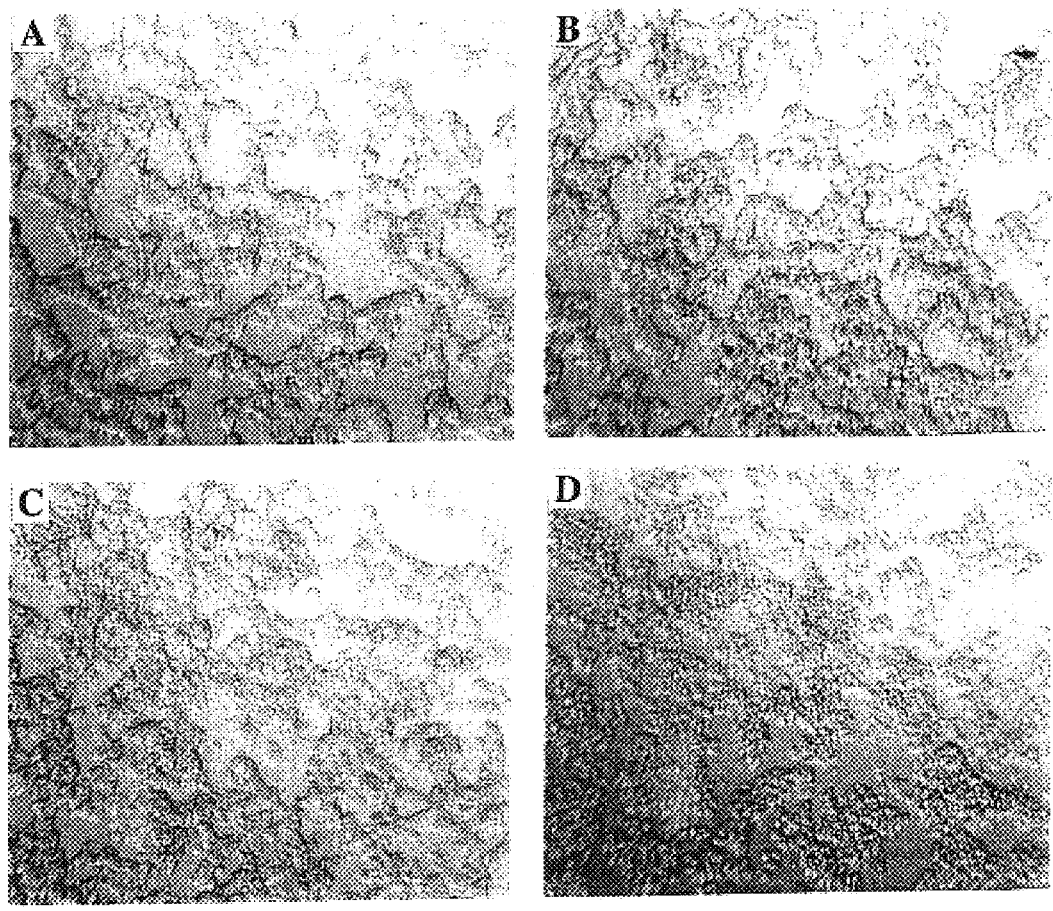
FIG. 7 is an image demonstrating in some embodiments of the invention that by doubling the amounts of cadmium/MT (from 60 to 120 µg/ml) and CCK3 (from 10 to 20 µM), the death of most ZR-75-1 cells occurred after treatments for 8 hours (D). Compared to the untreated control (A), single treatments with CCK3 (B) or cadmium/MT (C) failed to significantly alter cell morphology.

Cadmium/MT (120 μg/ml) Plus CCK3 (20 μM) Induce the Death of Estrogen Receptor Positive Human Breast Cancer ZR-75-1 Cells in 8 Hours Cells were cultured in triplicate in 12-well plates as described in Example 4. The ratio of cadmium and zinc in cadmium/MT was 5:1 per one MT molecule. ZR-75-1 cells were incubated in 10% serum-containing medium for 8 hours in the absence (FIG. 7A) or presence of 20 μM CCK3 (FIG. 7B), 120 μg/ml of cadmium/MT (FIG. 7C), or 120 μg/ml of cadmium/MT+20 μM CCK3 (FIG. 7D). The combination of cadmium/MT plus CCK3 effectively killed these cells after 8 hours treatment as judged from the strong morphological alteration of cells. In a similar experiment, the trypan blue exclusion assay confirmed that while CCK3 and cadmium/MT alone decreased viability only in 16 and 12% of cells, respectively, in combination they killed 100% of cells after treatments for 8 hours.

Example 10

Figure 8:
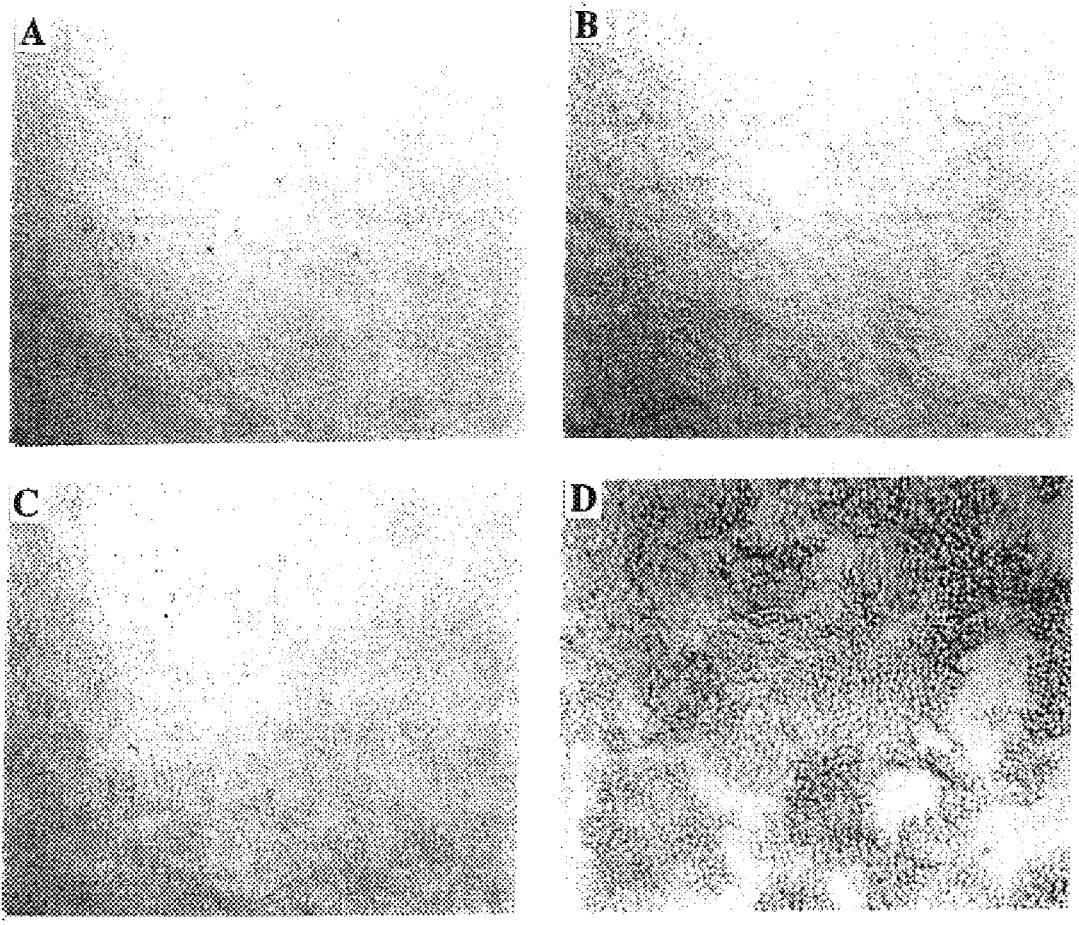
FIG. 8 is an image demonstrating in some embodiments of the invention that cadmium/MT (120 µg/ml) plus CCK3 (20 µM) induced the death of most estrogen positive human breast cancer MCF-7 cells in 8 h (D). Compared to the untreated control (A), single treatments with CCK3 (B) or cadmium/MT (C) failed to significantly alter cell morphology.

Cadmium/MT (120 μg/ml) Plus CCK3 (20 μM) Induce the Death of Estrogen Receptor Positive Human Breast Cancer MCF-7 Cells in 8 Hours The cells were cultured as described in Example 4. The ratio of cadmium and zinc in cadmium/MT was 5:1 per one MT molecule. MCF-7 cells were incubated in triplicates in 12-well plates in 10% serum-containing medium for 8 hours in the absence (FIG. 8A) or presence of 20 μM CCK3 (FIG. 8B), 120 μg/ml of cadmium/MT (FIG. 8C), or 120 μg/ml of cadmium/MT+20 μM CCK3 (FIG. 8D). The combination of cadmium/MT plus CCK3 effectively killed these estrogen receptor-positive human breast cancer cells after treatments for 8 hours as indicated by drastic changes in morphology. In a similar experiment, the trypan blue exclusion assay confirmed that while CCK3 and cadmium/MT alone had practically no effects on viability, in combination they killed 100% of cells after treatments for 8 hours.

Examples Showing that after Shorter-Term Treatments, the Same Amount of Cadmium/MT is More Effective than Zinc/MT in Killing Cancer Cells in the Presence of a Dithiocarbamate

Example 11

Figure 9:
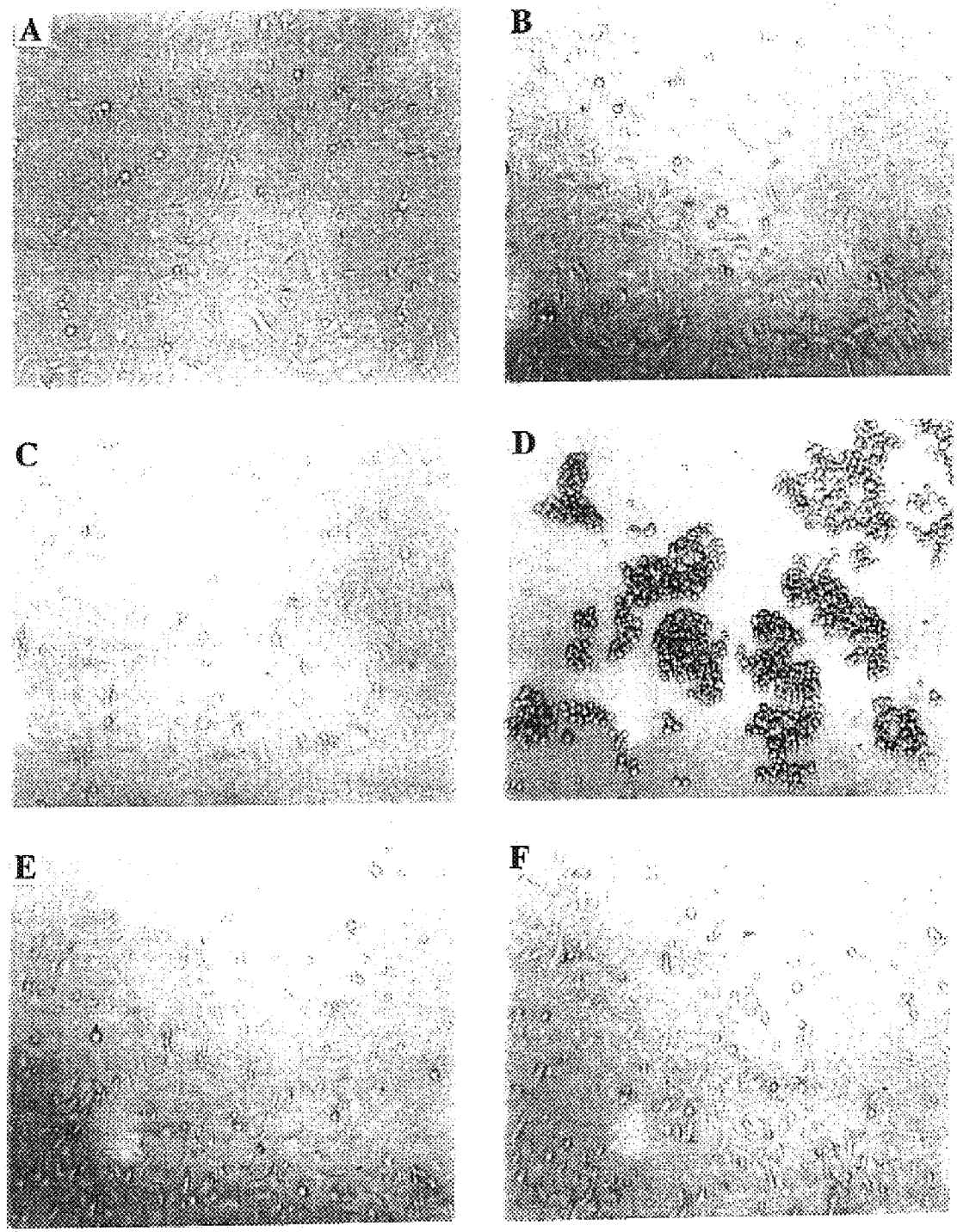
FIG. 9 is an image demonstrating in some embodiments of the invention that in the presence of PDC (20 µM), cadmium/MT (120 µg/ml) (D), but not zinc/MT (240 µg/ml) (F), induced the death of estrogen receptor negative human breast cancer MB-231 cells after the combined treatments for 8 hours. Compared to the untreated control (A), single treatments with PDC (B), cadmium/MT (C) or zinc/MT (E) were without effects on cell morphology.

Cadmium/MT (120 μg/ml), but not Zinc/MT (120 μg/ml), Induces the Death of Estrogen Receptor Negative Human Breast Cancer MB-231 Cells in the Presence of PDC (20 μM) in 8 Hours The cells were cultured as described in Example 4. The cadmium/MT contained 5 cadmium atoms per one MT molecule while zinc/MT contained 5 zinc atoms per one MT molecule. MB-231 cells were incubated in triplicate in 12-well plates in 10% serum-containing medium for 8 hours in the absence (FIG. 9A) or presence of 20 μM PDC (FIG. 9B), 120 μg/ml of cadmium/MT (FIG. 9C), 120 μg/ml of cadmium/MT+20 μM PDC (FIG. 9D), 120 μg/ml of zinc/MT (FIG. 9E), or 120 μg/ml of zinc/MT+20 μM PDC (FIG. 9F). The combination of cadmium/MT plus PDC, but not zinc/MT+PDC, effectively killed these cells after 8 h treatment as clearly indicated by the morphology of cells. In a similar experiment, the trypan blue exclusion assay confirmed that while 120 μg/ml of cadmium/MT+20 μM PDC killed 100% of cells, 120 μg/ml of zinc/MT+20 μM PDC decreased the viability of only ~18% of cells during the same period. In addition, cells treated with 120 μg/ml of cadmium/MT+20 μM PDC did not synthesize any DNA while treatment with 120 μg/ml of zinc/MT+20 μM PDC decreased DNA synthesis only by 32%. Thus, in this cell line cadmium/MT+PDC killed cells more rapidly and efficiently compared to the same amount of zinc/MT+PDC.

Example 12

Cadmium/MT (120 µg/ml), but not Zinc/MT (120 µg/ml), Induces the Death of Estrogen Receptor Positive Human Breast Cancer MB-468 Cells in the Presence of CCK3 (20 µM) in 8 Hours

Figure 10:
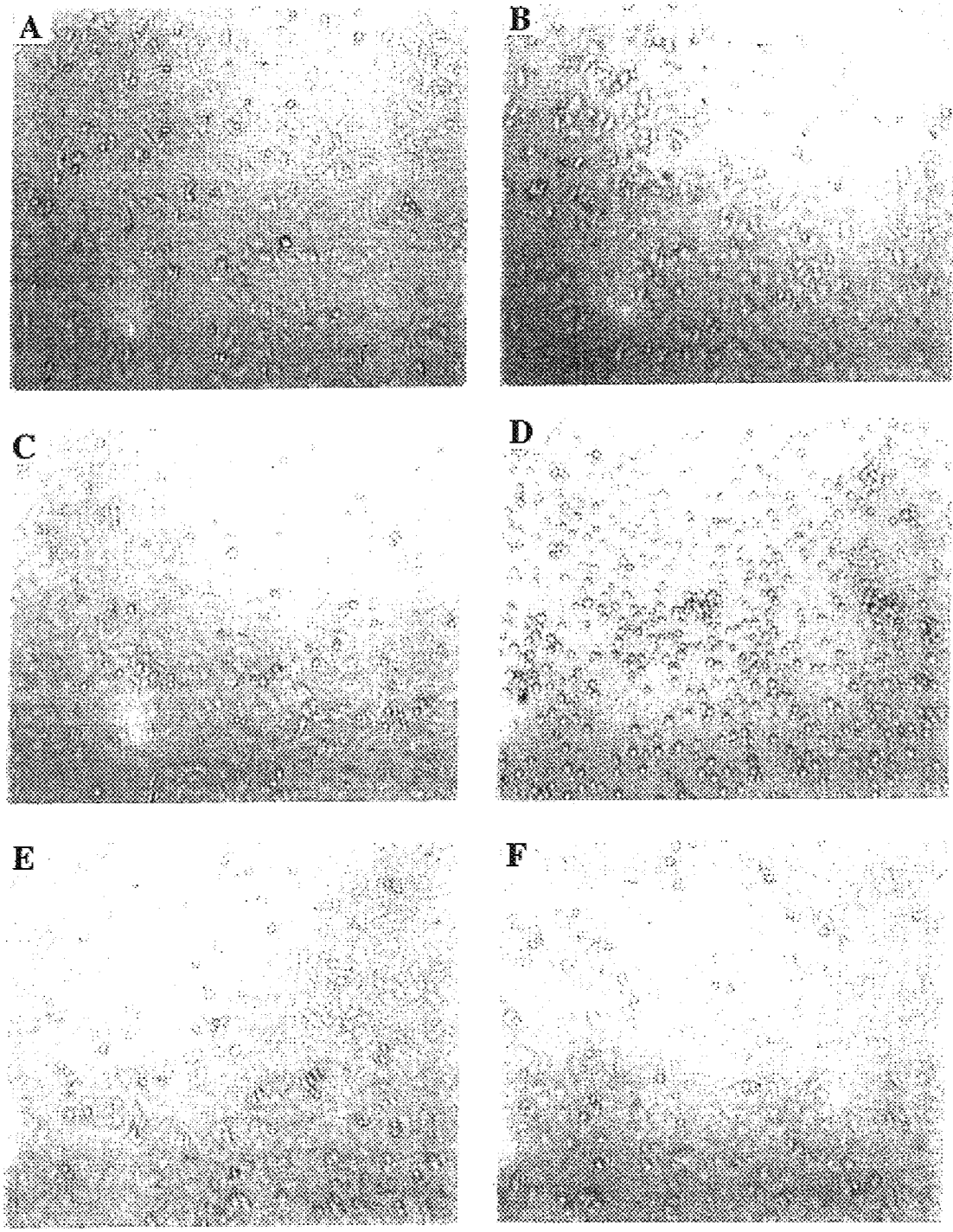
FIG. 10 is an image demonstrating in some embodiments of the invention that in the presence of PDC (20 μM), cadmium/MT (120 μg/ml) (D), but not zinc/MT (240 μg/ml) (F), induced the death of estrogen receptor positive human breast cancer MB-468 cells after the combined treatments for 8 hours. Compared to the untreated control (A), single treatments with PDC (B), cadmium/MT (C) or zinc/MT (E) were without effects on cell morphology.

The cells were cultured as described in Example 4. The cadmium/MT contained 5 cadmium atoms per one MT molecule while zinc/MT contained 5 zinc atoms per one MT molecule. MB-468 cells were incubated in triplicate in 12-well plates in 10% serum-containing medium for 8 hours in the absence (FIG. 10A) or presence of 20 µM CCK3 (FIG. 10B), 120 µg/ml of cadmium/MT (FIG. 10C), 120 µg/ml of cadmium/MT+20 µM CCK3 (FIG. 10D), 120 µg/ml of zinc/MT (FIG. 10E), or 120 µg/ml of zinc/MT+20 µM CCK3 (FIG. 10F). The combination of cadmium/MT plus CCK3, but not zinc/MT+CCK3, also effectively killed these cells after 8 hours of treatment. In a similar experiment, the trypan blue exclusion assay confirmed that while 120 µg/ml of cadmium/MT+20 µM CCK3 killed 100% of cells, 120 µg/ml of zinc/MT+20 µM CCK3 decreased the viability of cells only by ~16%.

Examples Showing that CCK3 in Combination with Cadmium/MTLP-25 or Zinc/MTLP-25 Effectively Kills Cancer Cells

Example 13

Cadmium/MTLP-25 or Zinc/MTLP in Combination with CCK3 Induce the Death of CaOV-3, T47D and PC-3 Cells

PC-3 human prostate adenocarcinoma cells were maintained and treated in Ham's F12K medium containing 7% fetal bovine serum. The CaOV-3 human ovarian adenocarcinoma cells were maintained and treated in Dulbecco's modified Eagle's medium containing 4 mM L-glutamine, 1.5 g/L sodium bicarbonate, 4.5 g/L glucose, 1 mM sodium pyruvate and 10% fetal bovine serum. T47D were maintained and treated in RPMI 1640 cell culture medium (see Gibco Catalogue) supplied with 2 mM L-glutamine, 10 mM Hepes, 1 mM sodium pyruvate, 4.5 g/L glucose, 1.5 g/L sodium bicarbonate, 0.2 I.U. bovine insulin/ml, and 10% fetal bovine serum. The cells were incubated in 96-well plates in the medium described above for 24 hours in the absence or presence of 20 µM CCK3 and/or 100 µg/ml of cadmium/MTLP-25 or 100 µg/ml of zinc/MTLP-25 as indicated in Table 1. After the treatment period, the MTT assay was used to determine the relative cell number of viable cells. Errors are expressed as S.D. (n=8 for each treatment). The data indicate that while CCK3 alone had no effects, in the presence of cadmium/MLTP-25 it reduced the viability of cancer cells by 75% or more. CCK3 had slightly smaller effects on cell viability in the presence of zinc/MTLP-25.

TABLE 1

Cadmium/MTLP-25 or zinc/MTLP in combination with CCK3 induce the death of CaOV-3, T47D and PC-3 cells.

| | Viability of cells (Absorbance; $A_{540}$) | | |
|---|---|---|---|
| Treatment | PC-3 | T47D | CaOV-3 |
| None | 2,660 ± 0.225 | 1,510 ± 0.155 | 1,500 ± 0.070 |
| CCK3 | 2,380 ± 0.270 | 1,435 ± 0.190 | 1,330 ± 0.115 |
| Cadmium/MTLP-25 | 1,270 ± 0.050 | 1,335 ± 0.275 | 0.890 ± 0.095 |
| CCK3 + cadmium/MTLP-25 | 0.290 ± 0.080 | 0.315 ± 0.080 | 0.280 ± 0.035 |
| Zinc/MTLP-25 | 2,480 ± 0.140 | 1,540 ± 0.225 | 1,420 ± 0.160 |
| CCK3 + zinc/MTLP-25 | 0.680 ± 0.180 | 0.540 ± 0.185 | 0.660 ± 0.080 |

The invention claimed is:

1. A multi-component pharmaceutical to induce cell death in tumors, the pharmaceutical comprising:

metal ions bound to a first carrier, wherein the first carrier is a protein comprising a minimum of four cysteine amino acids that non-covalently bind the metal ions in metal-thiolate clusters, wherein the first carrier is conjugated with one or more targeting molecules, the targeting molecules having a selective affinity for tumor cells, and wherein the first carrier is cell impermeable or slowly permeable; and a second carrier comprising a cell permeable dithiocarbonyl compound represented by the formula:

$(R_1)_m(R_2)Z-C-(S)-S-Y$ wherein:

m is 0 or 1;

$R_1$ and $R_2$ may be independently hydrogen or $C_1$-$C_{24}$ straight, branched, or cyclic alkyl, alkenyl, aryl, alkaryl, aralkyl, or alkoxy fragments, said fragments optionally substituted with ester, ether, halogen, ether, sulfate, hydroxyl, or phosphate groups or wherein $R_1$ and $R_2$ may be optionally connected via a bridge comprising —$(CH_2)_n$—, wherein n is 3-8, and wherein said bridge may be optionally substituted with $C_1$-$C_{10}$ straight, branched, or cyclic alkyl, aryl, aryalkyl, or alkaryl groups, each of said groups optionally substituted with hydroxyl, halo, phosphate, sulfate, or sulfonate groups;

Z is oxygen or nitrogen with the proviso that if Z is oxygen then m is 0; and

Y is hydrogen, $C_1$-$C_{12}$ amine, $C_1$-$C_{12}$ carboxyl, a pharmaceutically acceptable cation, a physiologically cleavable leaving group, a targeting moiety, or a chemotherapeutic drug;

wherein the second carrier has a greater affinity for the metal ions than the first carrier, wherein the second carrier transports the metal ions into the cell, and wherein the metal ions have sufficient kinetic lability with regard to the second carrier to allow transfer and release of the metal ions from the second carrier to an intracellular space to affect cell death; and wherein the first and second carriers are separate compositions.

2. The pharmaceutical of claim 1, wherein the first carrier is bound to three or more metal ions.

3. The pharmaceutical of claim 1 wherein the dithiocarbonyl compound is a dithocarbamate that binds the protein-derived metal ions in an exchangeable manner.

4. The pharmaceutical of claim 1 wherein the first carrier is a metallothionein.

5. The pharmaceutical of claim 1 wherein the first carrier comprises the amino acid sequence of: KDCGCSGASSC-NCGSGCSCSNCGSG (SEQ ID NO: 1).

6. The pharmaceutical of claim 1 wherein the metal ions are cadmium (II), zinc (II), copper (I), silver (I), cobalt (II), mercury (II), iron (II), gold (I), bismuth (III), nickel (II), lead (II), or platinum (II).

7. The pharmaceutical of claim 1 wherein the metal ion is cadmium (II).

8. The pharmaceutical of claim 1 wherein the metal ion is zinc (II).

9. The pharmaceutical of claim 1 wherein the second carrier is 3-aminopropylpiperidine-1-carbodithioate HCl.

10. The pharmaceutical of claim 1 wherein the second carrier is pyrrolidinedithiocarbamate.

11. The pharmaceutical of claim 1 wherein the targeting molecule is an antibody or antibody fragment, a receptor ligand, a receptor-binding fragment of epidermal growth factor, a lipid component of a targeted cell type, or a 3'-$NH_2$-modified nucleic acid ligand.

12. The pharmaceutical of claim 1, wherein the first carrier has polyethylene glycol attached thereto.

13. The pharmaceutical of claim 1 further comprising a nanoparticle or nanocell, the nanoparticle or nanocell comprising the targeting molecule.

14. The pharmaceutical of claim 13 wherein the nanoparticles or nanocells further comprise polyethylene glycol.

15. The pharmaceutical of claim 1, wherein the second carrier is conjugated to a targeting molecule, the targeting molecules having a selective affinity for tumor cells.

16. The pharmaceutical of claim 1, wherein $R_1$ and $R_2$ are connected via —$(CH_2)_n$—, wherein n is 3-8, to form a heterocycle.

17. The pharmaceutical of claim 1, wherein the targeting molecule is transferrin or folate.

* * * * *

UNITED STATES PATENT AND TRADEMARK OFFICE
CERTIFICATE OF CORRECTION

PATENT NO. : 7,655,620 B2
APPLICATION NO. : 11/472763
DATED : February 2, 2010
INVENTOR(S) : Zoltan Kiss It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this

Twenty-third Day of November, 2010

David J. Kappos
*Director of the United States Patent and Trademark Office*

SEQUENCE LISTING

<160> NUMBER OF SEQ ID NOS: 3

<210> SEQ ID NO 1
<211> LENGTH: 25
<212> TYPE: PRT
<213> ORGANISM: Artificial
<220> FEATURE:
<223> OTHER INFORMATION: Synthetic peptide

<400> SEQUENCE: 1

Lys Asp Cys Gly Cys Ser Gly Ala Ser Ser Cys Asn Cys Gly Ser Gly
1               5                   10                  15

Cys Ser Cys Ser Asn Cys Gly Ser Gly
            20                  25

<210> SEQ ID NO 2
<211> LENGTH: 9
<212> TYPE: PRT
<213> ORGANISM: Artificial
<220> FEATURE:
<223> OTHER INFORMATION: Synthetic peptide

<400> SEQUENCE: 2

```
Cys Gly Asn Lys Arg Thr Arg Gly Cys
1               5
```

```
<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Ala Ser Ser Ser Tyr Pro Leu Ile His Trp Arg Pro Trp Ala Arg
1               5                   10                  15
```